US006975894B2

(12) United States Patent
Wehrli et al.

(10) Patent No.: US 6,975,894 B2
(45) Date of Patent: Dec. 13, 2005

(54) DIGITAL TOPOLOGICAL ANALYSIS OF TRABECULAR BONE MR IMAGES AND PREDICTION OF OSTEOPOROSIS FRACTURES

(75) Inventors: Felix W. Wehrli, Bala Cynwyd, PA (US); Punam K. Saha, Philadelphia, PA (US); Bryon Roos Gomberg, Philadelphia, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 274 days.

(21) Appl. No.: 10/121,470

(22) Filed: Apr. 11, 2002

(65) Prior Publication Data

US 2002/0191823 A1 Dec. 19, 2002

Related U.S. Application Data

(60) Provisional application No. 60/283,270, filed on Apr. 12, 2001.

(51) Int. Cl.[7] ................................................ A61B 5/05
(52) U.S. Cl. ...................... 600/407; 600/410; 600/411; 600/416; 600/425; 378/21; 378/23; 378/27; 378/46; 378/47; 378/62; 378/4; 382/128; 382/131; 382/132
(58) Field of Search ................................ 600/425, 410; 378/21, 23, 27, 46, 47, 62, 4; 382/128, 131, 132

(56) References Cited

PUBLICATIONS

Gomberg, Bryon R; Saha, Punam K; Song, Hee Kwong, Scott N.; and Wehrli, Felix W., Topological Analysis of Trabecular Bone MR Images, Mar. 2000, IEEE Transactions on Medical Imaging, vol. 19, No. 3, p166–174.*

Gomberg, Bryon R; Saha, Punam K; Song, Hee Kwong, Scott N.; and Wehrli, Felix W.□□, Topological Analysis of Trabecular Bone MR Images, Mar. 2000, IEEE Transactions on Medical Imaging, vol. 19, No. 3, pp. 166–174.*
Aaron, et al., "Secondary osteoporosis and the microanatomy of trabecular bone," *Clin. Rheumatology* 8(S2):84–88 (1989).
Amling, M. et al., "Architecture and distribution of cancellous bone yield fracture clues. A histomorphometric analysis of the complete spinal column from 40 autopsy specimens," *Arch. Orthop, Trauma Surg.* 115:262–269 (1996).
Ciarelli, M. et al., "Evaluation of orthogonal mechanical properties and density of human trabecular bone from the major metaphyseal regions with materials testing and computed tomography,", *J. Orthopaedic Res.* 9:674–682 (1991).
Consensus development conference: diagnosis, prophylaxis, and treatment of osteoporosis. *Am. J. Med.* 94(6):646–650 (1993).

(Continued)

*Primary Examiner*—Brian L. Casler
*Assistant Examiner*—William C Jung
(74) *Attorney, Agent, or Firm*—Evelyn R. McConathy; Drinker Biddle & Reath

(57) ABSTRACT

The invention provides method, system and device for determining trabecular bone structure and strength by digital topological analysis, and offers, for the first time, a demonstration of superior associations between vertebral deformity and a number of architectural indices measured in the distal radius, thus permitting reliable and noninvasive detection and determination of the pathogenesis of osteoporosis. A preferred embodiment provides imaging in three dimension of a region of trabecular bone, after which the 3D image is converted into a skeletonized surface representation. Digital topological analysis is applied to the converted image, and each image voxel is identified and classified as a curve, a surface, or a junction; and then associated with microarchitectural indices of trabecular bone to quantitatively characterize the trabecular bone network. The invention is applicable in vivo, particularly on human subjects, or ex vivo.

19 Claims, 16 Drawing Sheets

(a)

(b)

OTHER PUBLICATIONS

DeHoff, R. et al., "Experimental determination of the topoliogical properties of three–dimensional microstructures," *J. Micro*scopy 95:69–91 (1972).

Durand, E. et al., "Cancellous bone structure: analysis of high–resolution CT images with the run–length method," *J. Comput. Assist. Tomogr.* 15:133–139 (1991).

Eastell, et al., "Classification of verbal fractures," *J. Bone. Miner. Res.* 6:207–215 (1991).

Feldkamp, L. et al., "The direct examination of three–dimensional bone architecture in vitro by computed tomography," *J. Bone Mineral Res.* 4:3–11 (1989).

Garrahan, N. et al., "A new method for the two–dimensional analysis of bone structure in human iliac crest biopsies.," *J. Microscopy*, 142:341–349 (1986).

Goldstein, S. et al., "Measurement and Significance of three–dimensional architecture to the mechanical integrity of trabecular bone," *Calcif. Tissue Internat'l* 53:S127–133 (1993).

Gomberg, B. et al., "Topological analysis of trabecular bone MR images," *IEEE Trans. Med. Imaging* 19(3) (2000A).

Gordon, C. et al., "In vivo assessment of trabecular bone structure at the distal radius from high–resolution computed tomography images," *Phys. Med. Biol.* 41:495–508 (1996).

Gordon, C. et al., "In vivo assessment of trabecular bone structure at the distal radius from high–resolution magnetic resonance images," *Med. Phys.* 24:585–593 (1997).

Gordon, C. et al., "Image–based assessment of spinal trabecular bone structure from high– resolution CT images," *Osteoporos Int.* 8(4):317–325 (1998).

Gordon, C. et al., "Relation between image–based assessment of distal radius trabecular structure and compressive strength," *Can. Assoc. Radiol. J.* 49:390–397 (1998).

Goulet, R. et al., "The Relationship between the structural and orthogonal compressive properties of trabecular bone," *J. Biomechanics* 27:375–389 (1994).

Gudbjartsson, H. et al., "The Rician distribution of noisy MRI data," *Magnetic Resonance Med.* 34:910–914 (1995).

Hahn, M. et al., "Trabecular bone pattern factor—a new parameter for simple quantification of bone microarchitecture," *Bone* 13:327–330 (1992).

Hildebrand, T. et al., "Quantificaton of bone microarchitecture with the structure model index," *Computer Meth. Biomech. Biomed. Engin.* 1:15–23 (1997).

Hildebrand, T. et al., "Direct three–dimensional morphometric analysis of human cancellous bone: microstructural data from spine, femur, iliac crest, and calcaneus," *J. Bone Miner. Res.* 14(7):1167–1174 (1999).

Hodgskinson et al., "Effects of structural variation on Young's modulus of non–human cancellous bone," *Proc. Inst. Mech. Eng.*, pt. H, 204:43–52 (1990).

Hwang, S. et al., "Probability–based structure parameters from 3D NMR images as predictors of trabecular bone strength," *Med. Phys.*, 24:1255–1261 (1997).

Hwang, S. et al., "Estimating voxel volume fractions of trabecular bone on the basis of magnetic resonance images acquired in vivo," *Internat'l Imaging Systems and Technol.* 10:186–198 (1999).

Hwang, S. et al., "Subvoxel processing: a new method for alleviating partial volume blurring in MR images of trabecular bone," *Proc. Internat'l Resonance in Medicine*, Eight Internat'l Meeting (Internat'l Soc. Magnetic Resonance in Medicine, Denver CO), pp. 2134 (2000).

Jensen, K. et al., "A model of vertebral trabecular bone architecture and it mechanical properites," *Bone* 11:417–423 (1990).

Kinney, J. et al., "The relationship between three–dimensional connectivity and the elastic properties of trabecular bone," *J. Bone Mineral Res.* 13:839–845 (1998).

Kleerekoper, M. et al., "The role of three–dimensional trabecular microstructure in the pathogenesis of vertebral compression fractures," *Calcif. Tissue Int.* 37:594–597 (1985).

Kong, T. et al., "Digital Topology: Introduction and Survey," *Computer Vision Graphics and Image Processing* 48:357–393 (1989).

Laib, A. et al., "Ridge number density: a new parameter for in vivo bone structure analysis," *Bone* 21(6):541–546 (1997).

Laib, A. et al., "In vivo high resolution 3D–QCT of the human forearm," *Tech. Health Care* 6(5–6):329–337 (1998).

Lane, N. et al., "Early estrogen replacement therapy reverse the rapid loss of trabecular bone volume and prevents further deterioration of connectivity in the rat," *J. Bone Miner. Res.* 14(2):206–214 (1999).

Legrand, E. et al., "Trabecular bone microarchitecture, bone mineral density and vertebral fractures in male osteoporosis," *J. Bone Miner. Res.* 15:13–19 (2000).

Link, T. et al., "In vivo high resolution MRI of the calcaneus: differences in trabecular structure in osteoporosis patients," *J. Bone Miner. Res.* 13(7):1175–1182 (1998).

Ma, J. et al., "Fast 3D large–angle spin–echo imaging (3D FLASE)," *Magnetic Resonance Med.* 35:903–910 (1996).

Majumdar, S. et al., "Correlation of trabecular bone structure with age, bone, mineral density, and osteoporotic status: in vivo studies in the distal radius using high–resolution magnetic resonance imaging," *J. Bone Mineral Res.* 12:111–118 (1997).

Majumdar, S. et al., "High–resolution magnetic resonance imaging: three–dimensional trabecular bone architecture and biomechanical properties," *Bone* 22(5):445–454 (1998).

Maunder, *Algebraic Topology*, Cambridge, UK: Cambridge Univ. Press, 1980.

Morita, M. et al., "Progression of osteoporosis in cancellous bone depending on trabecular structure,"*Ann. Biomed. Eng.* 22:532–539 (1994).

Mosekilde, L. "Age–related changes in vertebral trabecular bone architecture—assessed by a new method," *Bone* 9:247–250 (1988).

Mosekilde, L. "Consequences of the remodelling process for vertebral trabecular bone structure: a scanning electron microscopy study (uncoupling of unloaded structures," *Bone Mineral* 10(1):13–35 (1990).

Muller, R. et al., "Noninvasive bone biopsy: A new method to analyze and display the three–dimensional structure of trabecular bone," *Phys. Med. Biol.* 39:145–164 (1994).

Muller, R. et al., "In vivo reproducibility of three–dimensional structural properites of noninvasive bone biopsies using 3D–pQCT," *J. Bone Mineral Res.* 11:1745–1750 (1996).

Nelson, D. et al., "What is a Vertebral Fracture?" In: Marcus R, Feldman D, Kelsey J (eds.) *Osteoporosis*, Academic Press, San Diego, pp 613–621 (1996).

Oden, Z. et al., "The effect of trabecular structure on DXA–based predictions of bovine bone failure," *Calcif Tissue Int*, 63:67–73 (1998).

Odgaard, A. et al., "Quantification of connectivity in cancellous bone, with special emphasis on 3–D reconstructions," *Bone* 14:173–182 (1993).

Odgaard, A. et al., "Fabric and elastic principal directions of cancellous bone are closely realted," *J. Biomechan.* 30:487–495 (1997).

O'Neill, T. et al., "Definition and diagnosis of vertebral fracture," *J. Rheumatol.* 24(6):1208–1211 (1997).

Parfitt, A. "Stereologic Basis of Bone Histomorphometry: Theory of Quantitative Microscopy and Reconstruction of the Third Dimension," in *Bone Histomorphometry: Techniques and Interpretation*, R. R. Recker, Ed., Boca Raton, FL: CRC Press, 1981, pp. 53–87.

Parfitt, A. et al., "Relationships between surface, volume, and thickness of iliac trabecular bone in aging and in osteporosis. Implications for the microanatomic and cellular mechanisms of bone loss," *J. Clin. Invest.* 72:1396–1409 (1983).

Parfitt, A. "Implications of architecture for the pathogenesis and prevention of vertebral fracture," *Bone* 13:S41–47 (1992).

Peyrin, F. et al., "Micro–CT examinations of trabecular bone samples at different resolutions: 14, 7 and 2 micron level," *Technol. & Health Care* 6:391–401 (1998).

Pothuad, L. et al., "A new method for three dimensional skeleton graph analysis of porous media: application to trabecular bone microarchitecture," *J. Microsc.* 199:149–161 (2000).

Recker, R. "Architecture and vertebral fracture," *Calcif, Tissue Int.* 53 Suppl 1:S139–142 (1993).

Rosenfeld, A. "Adjacency in Digital Pictures," *Information and Control* 26:24–33 (1974).

Saha, P. et al., "3D digital topology under binary transformation with applications," *Computer Vision and Image Understanding* 63:418–429 (1996).

Saha, P. et al., "A new shape preserving parallel thinning algorithm for 3D digital images," *Pattern Recognition* 30:1939–1955 (1997).

Saha, P. et al., "Strongly normal sets of convex polygons or polyhedra," *Pattern Recognition Lett.* 19:1119–1124 (1998).

Saha, P. et al., "Determining simplicity and computing topological change in strongly normals partials tilings of $R^2$ and $R^3$," *Pattern Recongnition* 33:105–118 (2000A).

Saha, P. et al., "Three–dimensional digital topological characterization of cancellous bone architecture," *Internat'l J. Imaging Systems and Technology*, 11:81–90 (2000B).

Shrout, P. et al., "Intraclass correlations: Uses in assessing rate reliability," *Psychological Bull.* 86:420–428 (1979).

Stiffert, R. et al., "Dynamic relationshipd of trabecular bone density, architecture, and strength in a computational model of osteopenia," *Bone* 18:197–206 (1996).

Song, H. et al., "In vivo micro–imaging using alternating navigator echoes with applications to cancellous bone structural analysis," *Magnetic Resonance Med.* 41:947–953 (1999).

Steiner, E. et al., "Radiology of Osteoporosis," In: Marcus, R, Feldman D, Kelsey J (eds.) *Osteoporosis*, Academic Press, San Diego, pp. 1019–1050 (1996).

Udupa. J. et al., "Bourndary and object labelling in three–dimensional images," *Computer Vision Gaphics and Image Processing* 51:355–369 (1990).

Vesterby, A. "Star volume of marrow space and trabeculae in iliac crest: sampleing procedure and correlation to star volume of lumbar vertebra," *Bone* 11:149–155 (1990).

Vesterby, A. et al., "Biological meaningful determinants of the in vitro strength of lumbar vertebrae," *Bone* 12:219–224 (1989).

Wahner et al., *The Evaluation of Osteoporosis: Dual Energy X–ray Absorptiometry in Clinical Practice*, Cambridge: University Press, 1994.

Wehrli, F. et al., "Cancellous bone volume and structure in the forearm: noninvasive assessment with MR microimaging and image processing [published erratum appareas in *Radiology* Jun. 1998; 207(3):833]," *Radiology* 206:347–357 (1998B).

Wehrli, F. et al., "New architectural parameters derived from micro–MRI for the prediction of trabecular bone strength," *Technique Health Care* 6:307–320 (1998A).

Wehrli, F. et al., "Cross–Section study of osteopenia by quantitative magnetic resonance and bone densitometry," *Radiology* 217:527–538 (2000).

Wehrli, F. et al., "Digital topological analysis of in vivo MR microimages of trabecular bone reveals structural implications of osteoporosis," *J. Bone Mineral Research*, 16:8, 1520–1531 (2001).

Wessels, M. et al., "Connectivity in human cancellous bone by three–dimensional magnetic resonance imaging," *Medical Physics* 24:1409–1420 (1997).

WHO Technical Report Series No. 843, "Assessment of fracture risk and its application to screening for postmenopausal osteoporosis," World Health Organization, Geneva, 1994.

Wolff, *Das Gesetz der Transformation der Knochen* . Berlin: A Hirschwald, 1892.

Wu, Z. et al., "A Bayesian approach to subvoxel tissue classification in NMR microscope images of trabecular bone," *Magnetic Resonance Med.* 31:302–308 (1994).

* cited by examiner (a) (b)

(a) (b)

(a)  (b)  (c)  (d)

(a)　　　　　　　　(b)　　　　　　　　(c)

DIGITAL TOPOLOGICAL ANALYSIS OF TRABECULAR BONE MR IMAGES AND PREDICTION OF OSTEOPOROSIS FRACTURES

CROSS-REFERENCE TO RELATED APPLICATIONS

This application claims priority to U.S. Provisional Application No. 60/283,270 filed on Apr. 12, 2001.

GOVERNMENT SUPPORT

This work was supported in part by grants from the National Institutes of Health, grant numbers RO1 41443 and IT32-CA74781-02. The government may have certain rights in this invention.

FIELD OF THE INVENTION

This invention relates generally to the field of digital topological analysis (DTA) to derive structural parameters from trabecular bone images obtained by magnetic resonance imaging (MRI), computed tomography (CT), or other imaging technologies, and the use of these parameters to assess trabecular bone structure in patients at risk of developing fractures from osteoporosis or those suffering from metabolic bone disorders.

BACKGROUND OF THE INVENTION

Trabecular bone (TB) (also known as cancellous bone), which occurs in most of the axial skeleton and at locations toward the ends of the long bones, consists of a lattice of interconnected plates and rods that confer mechanical strength to the skeleton at minimum weight. In addition to the volume fraction of the trabecular bone (often quantified in terms of bone density), the three-dimensional (3D) arrangement of the trabecular network is a major determinant of elastic modulus (Odgaard et al., *J Biomechan.* 30:487–495 (1997)) and ultimate strength.

In general, characterization of the strength of trabecular lattices from three-dimensional (3D) images can be divided into three major categories: material, scale and topology (DeHoff et al., *J. Microscopy* 95:69–91 (1972)). 'Material properties' describe the bone material; 'scale properties' describe the size and thickness (local volume properties) of the trabecular elements; and the 'topological properties' describe the spatial arrangement of the bone material in the network. These parameters change characteristically with subject age. It is also widely accepted that the mechanical competence of trabecular bone (i.e., its resistance to fracturing) is a function of both mass density and architecture and that disease processes such as osteoporosis entail both loss in net bone mass and architectural deterioration (World Health Organization [WHO] Technical Report Series No. 843, 1994).

A common diagnostic screening method for osteoporosis is based on 'dual-energy X-ray absorptiometry' (DEXA) (Wahner et al., *The Evaluation of Osteoporosis: Dual Energy X-Ray Absorptiometry in Clinical Practice*, Cambridge: University Press, 1994) to measure integral bone mineral density (BMD). This method, however, does not distinguish between trabecular and cortical bone and ignores the role of structure as a contributor to mechanical competence.

It has been shown that the 3D arrangement (Mosekilde, *Bone* 9:247–250 (1988)) and the nature of the trabeculae (e.g., plate-like versus rod-like) (Morita et al., *Ann. Biomed. Eng.* 22:532–539 (1994)) can help explain the variation in elastic moduli and ultimate strength of trabecular bone networks that is unaccounted for by density alone (Ciarelli et al., *J. Orthopaedic Res.* 9:674–682 (1991); Goulet et al., *J. Biomechanics* 27:375–389 (1994)). In models of trabecular bone, Jensen et al. (*Bone* 11:417–423 (1990)) demonstrated that the apparent stiffness can vary by a factor of 5–10 when the arrangement of the network goes from a perfect cubic lattice to maximum irregularity, even though trabecular bone volume remains almost constant. The independent role of architecture in conferring strength to the trabecular network is supported by a large number of experimental studies (Gordon et al. (*Can. Assoc. Radiol. J.* 49:390–397 (1998); Oden et al. (*Calcif. Tissue Int.* 63:67–73 (1998); Siffert et al., *Bone* 18:197–206 (1996); Hwang et al., *Med. Phys.* 24:1255–1261 (1997)). It is generally agreed that 50%–60% of the mechanical competence of the bone can be explained by variations in the apparent density (bone mass/tissue volume). The clinical evidence for an independent contribution from trabecular architecture is equally compelling.

In the past, studies concerned with the quantitative description of trabecular bone have used histomorphometry from sections in conjunction with stereology to reconstruct the third dimension (Parfitt, In *Bone Histomorphometry: Techniques and Interpretation*, Boca Raton, Fla.: CRC Press, 1981, pp. 53–87 (1981)). Several studies involving histomorphometry in patients with and without vertebral fractures, matched for gender and BMD, found the two groups of subjects to differ in histomorphometric indices. Kleerekoper et al. (*Calcif Tissue Int.* 37:594–597 (1985)) first demonstrated that women with osteoporosis and vertebral compression deformities had a significantly lower mean trabecular plate density than did women without deformities, matched for age and BMD. Similarly, Recker (*Calcif Tissue Int.* 53 Suppl. 1:S139–142 (1993)) showed that a subset of patients with vertebral crush fractures, matched to an equal number of controls for trabecular bone volume, had considerably decreased trabecular plate density and increased marrow star volume (Vesterby et al., *Bone* 12:219–224 (1989)). Legrand et al. (*J. Bone Miner. Res.* 15:13–19 (2000)) studied 108 men with osteoporosis, of whom 62 had at least one vertebral fracture, and determined that the patients with fractures did not differ in age, bone mineral density of the spine or hip from those without fractures. However, trabecular number was lower and trabecular separation greater in the fracture group. Other distinguishing histomorphometric parameters were found to relate to network connectivity.

As pointed out, most measurements of trabecular architecture are based on two-dimensional (2D) images (Gordon et al., *Physics in Medicine and Biology* 41:495–508 (1996); Parfitt, 1981; Parfitt et al., *J. Clin. Invest.* 72:1396–1409 (1983); Vesterby, *Bone* 11:149–155 (1990); Hahn et al., *Bone* 13:327–330 (1992); Garrahan et al., *J. Microscopy.* 142:341–349 (1986)). Yet, it is well known that connectivity analysis of 2D sections does not accurately define the 3D structures found in trabecular bone networks (Odgaard et al., *Bone* 14:173–182 (1993). For example, what appears to be a rod in a 2D section, may actually be a cross-section of a plate-like structure in the 3D network, or even a junction between two plates. A 3D analysis is thus essential to unambiguously establish the topology of the trabecular architecture (Wessels et al., *Medical Physics* 24:1409–20 (1997)).

In vivo assessment of trabecular bone architecture can be achieved by computed tomography (Gordon et al., 1996;

Muller et al., *J. Bone Mineral Res.* 11:1745–1750 (1996); Laib et al., *Bone* 21(6):541–6 (1997); Laib et al., *Tech. Health Care* 6(5–6):329–337 (1998)), and magnetic resonance (MR) micro-imaging (Link et al., *J. Bone Miner. Res.* 13(7): 1175–1182 (1998); Majumdar et al., *Bone* 22(5): 445–454 (1998); Wehrli et al., *Techn. Health Care* 6:307–320 (1998A)). Studies performed in patients are usually conducted at peripheral skeletal locations, such as the wrist (Majumdar et al., *J. Bone Mineral Res.* 12:111–118 (1997); Gordon et al., *Med. Phys.* 24:585–593 (1997); Wehrli et al., *Radiology* 206:347–357 (1998B)) and have been shown useful in deriving trabecular structural quantities. Recent advances have permitted analysis of the resulting images by probability-based image processing techniques (Hwang et al., *Internat'l J. Imaging Systems and Technol.* 10:186–198 (1999)).

One potentially powerful approach toward characterizing and quantifying trabecular network architecture is based on topological evaluation of the structure. Topology is the branch of mathematics concerned with the geometric properties of deformable objects (that are invariant in scale, rotation and translation) (Maunder, *Algebraic Topology*, Cambridge, UK: Cambridge Univ. Press, 1980). For example, topological criteria allow a determination as to whether a particular point in the network is part of a surface, curve, or junction. To illustrate the difference between topology and scale, one can consider a trabecular bone network that undergoes slight uniform thickening. Topologically, the network remains unaltered, but the scale properties have changed, which will result in changes to the mechanical properties. Conversely, given two networks with identical 'bone volume fraction' (BV/TV), one with more plate-like trabecular bone is assumed to be stronger than one that has trabeculae that are more rod-like. Here, the two networks differ in topology.

Feldkamp et al. (*J. Bone Mineral Res.* 4:3–11 (1989)) were among the first to use topological measures to describe trabecular lattices from 3D images obtained by micro-CT ($\mu$-CT) images. The investigators reasoned that connectivity is impossible to derive from images of two-dimensional sections, hence they expressed connectivity in terms of a global network, referred to as the Euler characteristic or number. The Euler characteristic, derived from the Euler-Poincaré formula, assumes the number of bone objects to be one, and that marrow cavities do not exist in the network. These assumptions make the Euler characteristics equivalent to the first Betti number (Feldkamp et al., 1989), which is a measure of the number of loops in the network. This approach permitted characterization of osteoporotic changes in laboratory animals, demonstrating that the reduction in connectivity following bone loss and recovery parallels the reduction in Young's modulus for loading (Kinney et al., *J. Bone Mineral Res.* 13:839–845 (1998)).

Lane et al. (*J. Bone Miner. Res.* 14(2):206–214 (1999)) showed that ovariectomized rats, when treated with estrogen, could restore their pre-ovariectomy bone volume, but not the lost connections, thus demonstrating the disparate behavior of bone volume fraction and network topology. Pothuaud et al. (*J. Microsc.* 199:149–161 (2000)), extended the classical approach toward establishing topological quantities, such as the Euler-Poincaré number, with counts of branches and termini on the basis of skeleton graphs.

However, classical topology in terms of the Euler number ignores the existence of plates and rods, and fails to provide information on the spatial distribution of connectivity. Moreover, it may fail to detect the effect of osteoporotic erosion, as has been pointed out by Kinney et al., 1998. The first Betti number is inherently insensitive to trabecular erosion, which is known to result in perforation of trabecular bone plates and disconnection of rod-like trabecular bone (Amling et al., *Arch. Orthop. Trauma Surg.* 115:262–269 (1996); Parfitt, *Bone* 13:S41–47 (1992)). The First Betti number cannot distinguish between perforation of trabecularbone plates and disconnection of rods. The first Betti number will decrease from loss of rods, causing a reduction in the number of loops. However, it would increase as a result of perforation of plates, which increases the number of loops. Therefore, the first Betti number can not necessarily detect osteoporotic bone erosion.

Various approaches have been described to distinguish rod-like from plate-like architectures. Hahn et al., 1992, found the proportion of trabecular plates to rods to be reflected by the ratio of concave to convex surfaces, expressed in terms of the 'trabecular bone pattern factor.' An algorithm making use of the change in surface area for a differential change in radial expansion, led to the definition of a parameter denoted 'structure-model index' (SMI) Hildebrand et al., *Computer Meth. Biomech. Biomed. Engin.* 1:15–23 (1997). This metric was subsequently applied to the quantitative characterization of 3D $\mu$-CT trabecular bone images from multiple anatomic locations known to be predominantly plate-like (SMI 0–1) or rod-like (SMI 2–3) (Hildebrand et al., *J. Bone Miner. Res.* 14(7):1167–1174 (1999)).

Nevertheless, none of the existing methods provide a reliable and efficient method for quantitatively characterizing the 3D architecture of cancellous bone networks, which are highly dependent on structural organization. Nor does the prior art provide methods for assessing bone strength or for predicting fracture risk in vivo in patients suffering from osteoporosis or metabolic bone disorders. It is an object of the present invention to meet these needs.

SUMMARY OF THE INVENTION

The present invention comprises a method, system and device for noninvasively detecting bone structure. The method is based on digital topological analysis (DTA), which was first theoretically considered by one of the inventors (Saha et al., *Computer Vision and Image Understanding* 63:418–429 (1996)). DTA classifies each voxel in a 3D structure, based on the connectivity information of the neighboring voxels. In the present invention, however, DTA is shown to completely characterize trabecular bone networks by unambiguously establishing the topological class of each voxel in digital images of trabecular bone. Images suited for analysis by the present invention include those obtained by magnetic resonance (MRI), X-ray computed tomography (CT) or other imaging modalities, including 3D images reconstructed from serial sectioning of specimens.

The embodied method provides insight into the pathogenesis of osteoporosis, i.e., the conversion of plates to rods and the disruption of the rod-like trabecular elements. It also provides the reproducibility necessary to evaluate the progression of disease or its regression in response to treatment. Image-derived topological parameters have been shown to discriminate groups of patients with osteoporotic fractures, from those without fractures. Fractures refer to any fracture caused by compromised structure secondary to bone disease including but not limited to fractures of the femur, forearm, humerus, tibia, vertebrae and ribs. Rods and plates refer to the gray scale image representations of trabecular structures, and curves and surfaces refer to their surface skeleton counterparts.

Typically, structure is measured at a peripheral site in the appendicular skeleton (radius, tibia, calcaneus) serving as a 'surrogate site' to predict structure at the fracture site but future embodiments will target the potential fracture site directly. The process entails imaging in three dimensions a region of trabecular bone (or using a pre-existing image); converting the 3D image, after binarization, into a skeletonized surface representation consisting of only 1- and 2-dimensional structures; and classifying each image voxel as a curve, a surface, or a junction; and deriving microarchitectural indices of trabecular bone to quantitatively characterize the trabecular bone network. In a preferred embodiment the method is combined with the measurement of scale parameters, such as trabecular bone volume fraction or thickness as a means to assess the network strength of the bone, and patients' risk of sustaining fractures. The method is applicable to, e.g., cadaver specimens or biopsies, or in vivo, in human subjects or laboratory animals.

The method has been validated with synthetic images and applied to a range of MR images of human trabecular bone obtained in two resolution regimens: (1) at high resolution in cadaveric specimens and (2) at lower resolution in vivo. The algorithm of the invention has been shown to be robust over a wide range of resolutions. Variations have been in good qualitative agreement with the visual appearance of the different morphologies, as long as image voxel size was sufficient to resolve the structures under investigation. Applications to 3D MR microimages of trabecular bone from the human distal radius indicate that the volume densities of topological parameters, such as the surface-to-curve ratio, are strong predictors of Young's modulus. Analysis of in vivo MR microimages from the human wrist further indicate that topological parameter densities vary substantially among subjects, even though bone mineral densities do not distinguish them.

Since each voxel is classified uniquely, a preferred embodiment of the invention topological classification of the distal radius, used as a surrogate site, offers a method for predicting the risk of potential fractures in patients predisposed toward osteoporosis. In another preferred embodiment, the steps for determining the structure of the patient's trabecular bone network are repeated at periodic intervals, and the resulting determinations are compared to measure the progression or regression of osteoporosis in the patient. Such longitudinal studies can be used to study disease etiology and therapy response, where a patient has to be examined repeatedly during the course of treatment. Drugs that might be studied in such a manner can include, but are not limited to, anabolic drugs (estrogen, testosterone, parathyroid hormone) or antiresorptives (osteoclast inhibitors).

To further demonstrate the effectiveness of the method, digital topological analysis was used to quantify the architecture of the trabecular bone network in the distal radius of patients of widely varying bone density using 3D $\mu$-MRI, and the findings were compared with DEXA BMD. Specifically, structural indices in the distal radius, although associated with BMD in the proximal femur and spine, provided information not available from bone densitometry, and established the distal radius as an appropriate surrogate site for probing the architectural changes that are known to accompany bone loss in the vertebrae during osteoporosis. Thus, an embodiment of the invention provides a method for measuring the progression or regression risk of osteoporosis in the patient, while another provides a method, wherein the risk of potential osteoporotic fractures in the patient are assessed.

The invention further provides a system for noninvasively determining bone structure and strength by digital topological analysis, comprising: means for acquiring or reading a 3D image of a region of trabecular bone; means for converting the 3D image into a skeletonized surface representation; means for analyzing the converted image by digital topological analysis; means for identifying and classifying each image voxel as a curve, a surface, or a junction; and means for associating the classified image with microarchitectural indices of trabecular bone to quantitatively characterize the trabecular bone network.

The invention also provides a device for noninvasively determining bone structure and strength by digital topological analysis, comprising: a computer-readable signal-bearing medium leans in the medium for converting the 3D image into a skeletonized surface representation; means in the medium for analyzing the converted image by digital topological analysis; means in the medium for identifying and classifying each image voxel as a curve, a surface, or a junction; and means in the medium for deriving from the classified image microarchitectural indices of trabecular bone to quantitatively characterize the trabecular bone network.

The system and the device are each effectively used on a patient or ex vivo.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentality shown.

In FIG. 2(a) B$\Re$ forms one tunnel and S$\Re$-B$\Re$ generates exactly two components. In FIG. 2(b) B$\Re$ forms two tunnels and S$\Re$-B$\Re$ generates exactly three components.

In FIG. 3(a), a marrow path (shown by semitransparent voxels) is shown crossing a closed bone path on the boundary of a 3×3×3 cube. In FIG. 3(b), Y(p) is shown. Notably, no marrow path of Y(p) crosses the closed bone path.

FIG. 5(a) exemplifies continuous 3-space $\Re^3$. FIG. 5(b) exemplifies digital space.

FIG. 6(a) depicts a structure resulting in profile elements. FIG. 6(b) depicts classification of profile elements (shown by dotted voxels); all others voxels are classified as curve elements.

In FIG. 8(a) and 8(b) the SS-line was obtained using Tables 1 and 2. In FIGS. 8(c) and 8(d) the SS-line is shown after the extension process.

FIG. 13(a) depicts a highly rod-like network. FIG. 13(b) depicts a medium rod-like network. FIG. 13(c) depicts a highly plate-like network. FIG. 13(d) depicts a very highly plate-like network.

In FIG. 15(b) the model used was an inverse relationship (hyperbola) between the two parameters compared.

FIG. 16(a) shows the topological surface-to-curve ratio (mean p=0.01); FIG. 16(b) shows discriminators of fracture (mean p=0.0004).

DESCRIPTION OF PREFERRED EMBODIMENTS OF THE INVENTION

The invention relates generally to the field of digital topological analysis (DTA) to derive structural parameters from trabecular bone images obtained by magnetic resonance imaging (MRI), CT, or other image technologies, such as serial sectioning; and to the targeted use of these parameters, including assessment of disease severity and risk of fracture from bone diseases, including, but not limited to, osteoporosis (postmenopausal, senile, corticosteroid and disuse), hyperparathyroidism, hyperthyroidism, Paget's disease, osteomalacia and renal osteodystrophy.

Topological Theory

The basis of digital topology relies on calculating the number of objects, tunnels, and cavities in the immediate neighborhood of each bone voxel. However, before proceeding further, it is essential to first understand the mathematical basis of digital topological analysis in the context of trabecular bone images. Most digital imaging systems produce images on a rectangular grid where the basic image elements, referred to as "spels," are hypercuboids. The term "spels" is an abbreviation for spatial elements; in 2D spels are 'pixels,' while in 3D they are 'voxels.' Mathematically, this is explained by letting n-dimensional Euclidean space $\Re^n$ be divided into hyper cuboids by n orthogonal families, each of equally distant parallel planes. The following mathematical symbols are used to describe the invention: $\in$ means 'element of;' $\cap$ means 'intersection of;' $\exists$ means 'there exists;' and $|x|$ means 'Euclidean norm of x.'

Digital topology deals with 'binary images,' which are herein defined as 3D matrices of voxels whose positions are represented by a vector of Cartesian coordinates, $x=(x_1, x_2, x_3)$, and whose voxels can have only one of two values, bone or marrow. Such an image is usually obtained by binarizing a gray-scale intensity image, such as an image wherein the intensities represent the bone volume fraction (BVF) occupied by each voxel.

Figure 1:
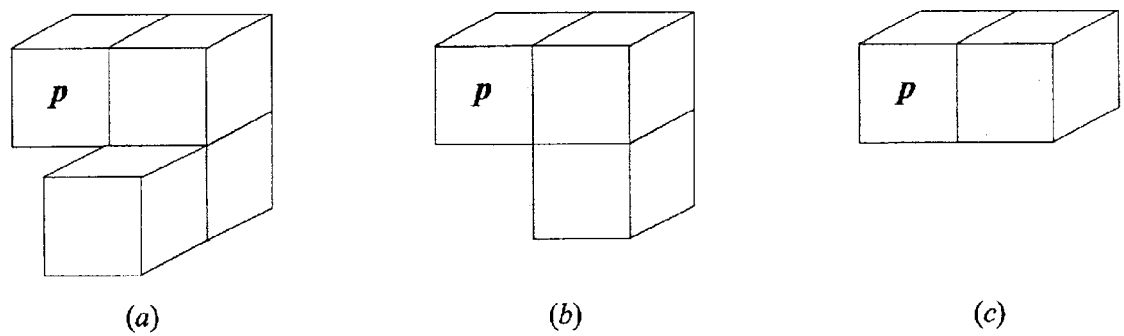
FIGS. 1(a)–1(c) are diagrams depicting 26-, 18-, and 6-adjacencies (shown in FIG. 1(a), FIG. 1(b), and FIG. 1(c), respectively) in a cubic grid.

Two voxels x and y are called '6-adjacent' if $|x-y|=1$ (face adjacent only); '18-adjacent' if $|x-y| \leq \sqrt{2}$ (face and edge adjacent); and '26-adjacent' if $|x-y| \leq \sqrt{3}$ (face, edge and corner adjacent), see e.g., FIG. 1. As shown, higher order adjacencies (i.e., 26-adjancency) include the lower order adjacencies (i.e., 6- or 18-adjancency).

When considering binary images, the voxels are separated into two sets, one for bone (foreground) and one for marrow (background). Let S be a non-empty set of bone voxels, such as all the bone voxels in a 3D digital image (a binary image). An 'α-path' (where a can be 6, 18 or 26) between two voxels p, q∈S means a sequence of voxels $p_0, p_1, \ldots, p_n$ ($p=p_0$ and $q=p_n$) in S such that $p_i$ is α-adjacent to $p_{i+1}$, $0 \leq i < n$. An α-path is an 'α-closed path' if $p_0$ is α-adjacent to $p_n$. Two voxels p, q∈S are 'α-connected' in S if there exists an α-path from p to q in S. An 'α-object' of S is a maximal subset of S, where each pair of voxels is α-connected. A set of voxels is 'simply connected' if it is connected, but contains no tunnel.

To satisfy the Jordan curve theorem, bone objects are defined as 26-objects of bone voxels (i.e., 26-connected), and marrow objects (background) are 6-objects of marrow voxels (Rosenfeld, *Information and Control* 26:24–33 (1974); Kong et al., *Computer Vision Graphics and Image Processing* 48:357–393 (1989)).

In general, cavities are marrow objects surrounded by bone. Since physiologically the entire marrow space in trabecular bone is connected, no such cavities exist in reality. However, to determine the local neighborhood connectivity, the central bone voxel is considered a marrow voxel (described below) which, technically, could result in a single voxel cavity. For example, when three straight, orthogonal, 6-connected bone curves intersect, the voxel at the intersection forms a single-voxel cavity because all of its 6-neighbors are bone voxels.

Although tunnels are easily visualized and intuitively described, they are difficult to formally define. However, the number of tunnels in an object can be defined precisely. Intuitively, a tunnel would be the handle of a coffee mug, formed by bending a cylinder to connect the two ends to each other or to a single connected object. There exists a connection between tunnels and handles, such that when the coffee mug's handle is broken, the tunnel is lost. A handle is an object that can be elastically deformed to a simple, closed curve. In most objects, the number of tunnels can be counted by recursively reducing the number of handles. If the object has a cavity that forms a handle (e.g., the interior of a hollow torus), this cavity must first be filled, and then the exterior handles counted. For example, a ring has one tunnel because the object forms a single solid handle. A hollow torus has two tunnels: the first arises from the cavity inside the ring and the second from the ring itself. More accurately, the number of tunnels in an object is the rank of its first homology group (Kong et al., 1989). The number of objects, tunnels, and cavities represent the $0^{th}$, $1^{st}$, and $2^{nd}$ Betti numbers, respectively.

In the following discussions, for any bone voxel p, N(p) denotes the set of 27 voxels in the 3×3×3 neighborhood of p (including the central voxel p) and N*(p) denotes the set of 26 voxels in the 3×3×3 neighborhood of p (excluding p, that is, p is considered marrow). Because the bone structure of N(p) always contains exactly one simply connected object without cavities (Saha et al., *Pattern Recognition Lett.* 19:1119–1124 (1998)), the topological properties of N(p) are invariant and N*(p) must be used to characterize the local topology. Let $\xi(p)$, $\eta(p)$, and $\delta(p)$, respectively, denote the number of objects, tunnels, and cavities in the bone structure of N*(p). Then, $\xi(p)$, $\eta(p)$, and $\delta(p)$ are called the local topological parameters of p. Let X(p) and Y(p) be the sets of 6- and 18-adjacent marrow voxels top, respectively. It may be noted that a marrow object in Y(p) can be either 6- or 18-adjacent top, depending on whether or not it intersects X(p).

The following two theorems (Saha et al., *Pattern Recognition* 33:105–118 (2000A), herein incorporated by reference) provide a computational definition of $\eta(p)$, and $\delta(p)$ in the bone structure of N*(p), while the number of objects can be computed using standard algorithms (Udupa et al., *Computer Vision Graphics and Image Processing* 51:355–369 (1990)):

Theorem 1. If X(p) is nonempty, the number of tunnels, $\eta(p)$ is one less than the number of marrow objects of Y(p) that intersects X(p), and zero otherwise.

Theorem 2. The number of cavities, $\delta(p)$, is one when all the 6-neighbors of p are bone voxels and zero otherwise.

Figure 2:
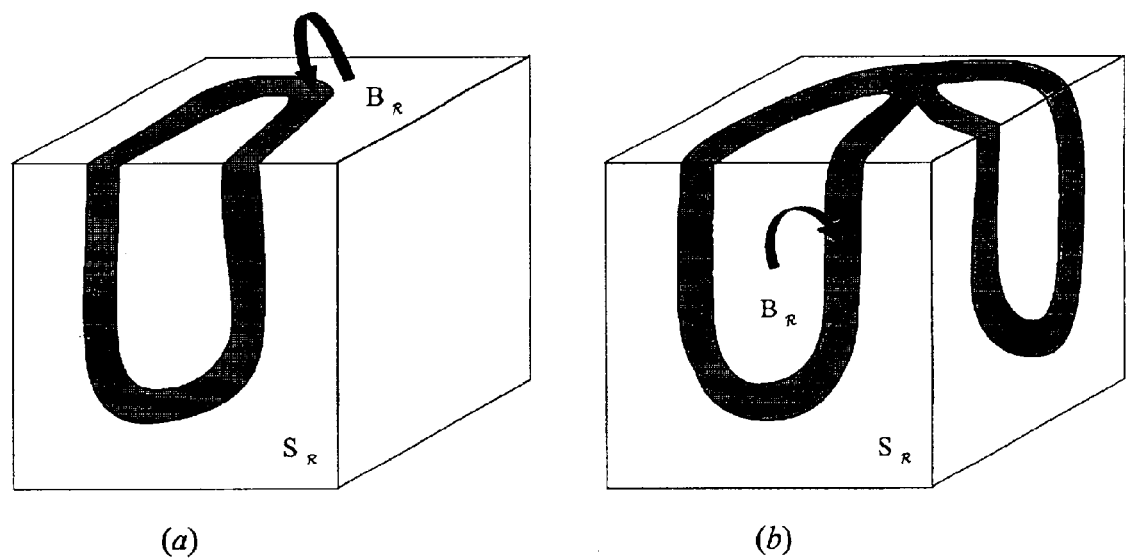
FIGS. 2(a) and 2(b) are diagrams depicting tunnels on the boundary of a topological ball.

Whereas Theorem 2 is trivial, Theorem 1 needs some clarification. In the continuous topological space, $\mathfrak{R}^3$, a topological sphere, $S\mathfrak{R}$, is any object that can be elastically deformed to the boundary of a solid ball (e.g., the surface of a brick). Following the Jordan curve property, a subset, $B\mathfrak{R}$, of such a sphere forms a tunnel if $B\mathfrak{R}$ forms a loop, and therefore disconnects $S\mathfrak{R}$ into several objects, i.e., $S\mathfrak{R}$-$B\mathfrak{R}$ has more than one object. If $S\mathfrak{R}$-$B\mathfrak{R}$ is empty, there is no tunnel; otherwise, the number of tunnels is one less than the number of objects in $S\mathfrak{R}$-$B\mathfrak{R}$, as shown in FIG. 2.

In FIGS. 2(a) and 2(b), $B\mathfrak{R}$ forms 1 and 2 tunnels, respectively. Thus, it may be seen that in FIGS. 2(a) and 2(b), $S\mathfrak{R}$-$B\mathfrak{R}$ has two and three objects, respectively. When applied to digital topology, the sphere is N*(p), and subset, B (analogous to $B\mathfrak{R}$ in continuous space), is the set of bone voxels in N*(p). N*(p)−B is the set of marrow voxels on the digital sphere. The number of tunnels in N*(p) is, therefore, one less than the number of marrow objects in N*(p), after the following two important considerations.

The first consideration has to do with the marrow objects that can contribute a tunnel. To form a tunnel, the marrow object must be adjacent to the interior of the sphere (i.e., p in the digital space). Therefore, the marrow objects in N*(p) that are not 6-adjacent top cannot contribute a tunnel, and only the marrow objects that intersect X(p) are considered. The second consideration is that the corners of N*(p) must be excluded from the set of marrow voxels to be able to apply the Jordan curve theorem on a digital sphere, that is, a closed curve on a sphere must divide it into two objects. This means that a ring of bone voxels on N*(p) should always disconnect N*(p) into two objects.

Figure 3:
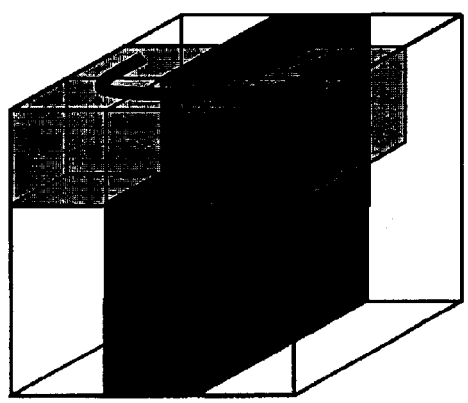
FIGS. 3(a) and 3(b) are diagrams depicting tunnels on the boundary of a digital 3×3×3 cube. Bone voxels are shown dark; marrow voxels are shown transparent and semitransparent in FIG. 3(a) and opaque in FIG. 3(b). In both FIGS. 3(a) and 3(b), bone voxel configurations are the same.
Figure 3:
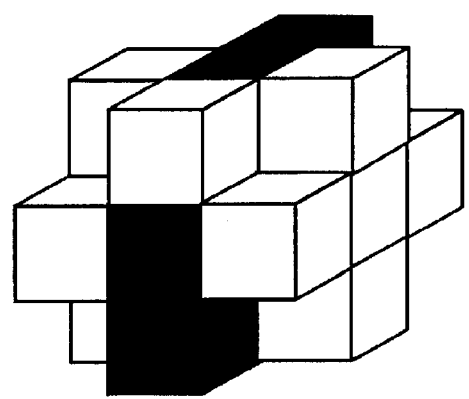

As shown in FIG. 3, the ring of bone voxels form a loop, but they do not disconnect the marrow "shell" into two marrow objects because a 6-path of marrow voxels (shown by arrow) exists between the two supposedly disconnected marrow objects (to left and right of the loop). The 6-path of marrow voxels crosses the loop of bone voxels on the digital closed surface of N*(p), creating an anomaly of the Jordan curve property in digital space. By excluding the corners of N*(p) from the marrow objects, marrow paths are not permitted to cross a loop of bone voxels, and therefore, from joining separate marrow objects (FIG. 3(b)). Therefore, Y(p) includes only the marrow voxels that are 18-adjacent top. Rigorous proof of these theorems can be found in Saha et al., 2000A.

An Efficient Method of Computing $\xi(p)$, $\eta(p)$, and $\delta(p)$.

Figure 4:
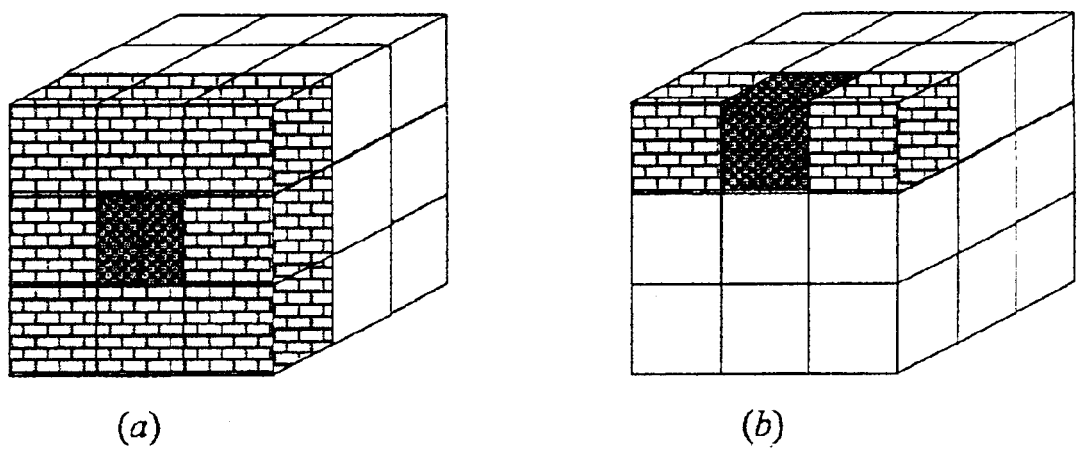
FIGS. 4(a) and 4(b) are diagrams depicting the faces and edges of N*(p). Voxels on a face in FIG. 4(a), or on an edge in FIG. 4(b) are shown in a light gray pattern, while the representative voxels are shown in a dark gray pattern.

A 'face' of N*(p) is the set of 3×3 voxels, all being at the same side of N*(p). The unique 6-neighbor on a face of N*(p) will be referred to as the representative voxel of that face. Similarly, an edge of N*(p) is the set of three voxels, all being at the intersection of two faces of N*(p). The unique 18-neighbor on an edge of N*(p) will be referred to as the representative voxel of that edge. A face and an edge of N*(p) along with their representative voxels are shown in FIG. 4. The method of computing topological parameters is primarily built on the following theorem, for which rigorous proof can be found in Saha et al., 2000A.

Theorem 3. When the representative voxel of a face or an edge is bone, the topological parameters $\xi(p)$, $\eta(p)$, and $\delta(p)$ are independent of the other voxels in that face or edge.

A face or an edge of N*(p) can be called dead if its representative voxel is a bone voxel. Otherwise, the voxels of that face or edge may contribute to the local topological parameters of N*(p). A voxel is called 'effective' if it does not lie on a dead face or edge. To determine $\xi(p)$, $\eta(p)$, and $\delta(p)$, it is sufficient to know the configuration of effective voxels. After determining the configuration of all 6-neighbors, the algorithm computes the topological parameters using a lookup table of effective voxel configurations.

There are 64 possible configurations of 6-neighbors. However, these configurations can be grouped based on the relative positions of bone 6-neighbors. A geometric class of N*(p) is a set of all 6-neighbor configurations that are equivalent under orthogonal symmetry operations. The computations of topological parameters for all 6-neighbor configurations in the same geometric class are identical. There are 10 possible geometric classes in N*(p):

Class 0: All 6-neighbors are bone. Number of effective voxels ($n_e$)=0.

Class 1: Five 6-neighbors are bone. $n_e$=0.

Class 2: Two pairs of opposite 6-neighbors are bone. $n_e$=0.

Class 3: One pair of opposite, and two non-opposite 6-neighbors are bone. $n_e$=1.

Class 4: One pair of opposite, and another 6-neighbors are bone. $n_e$=2.

Class 5: Three non-opposite 6-neighbors are bone. $n_e$=4.

Class 6: One pair of opposite 6-neighbors is bone. $n_e$=4.

Class 7: Two non-opposite 6-neighbors are bone. $n_e$=7.

Class 8: Only one 6-neighbor is bone. $n_e$=12.

Class 9: No 6-neighbor is bone. $n_e$=20.

For geometric Classes 0–2, there is no effective voxel and the parameters are immediately known. For example, in Class 2, $\xi(p)=1$, $\eta(p)=1$, and $\delta(p)=0$. Except for Class 9, there are only a few effective voxels. A straightforward lookup table can be used that provides the values of $\xi(p)$, $\eta(p)$, and $\delta(p)$, for every effective voxel configuration. The efficiency of Class 9 can be improved by dividing it into two subcases: (1) all edge-adjacent (i.e., 18-adjacent but not 6-adjacent) neighbors are marrow, in which case, $\xi(p)=\eta(p)=0$, and $\delta(p)$ equals the number of bone voxels in $N^*(p)$, and (2) at least one edge-adjacent neighbor is bone, in which case the number of effective voxels is 17. Note that the two vertex-adjacent (i.e., 26-adjacent but not 18-adjacent) neighbors on the dead edge are no longer effective, and that the configuration of the bone edge neighbor is already known. At this stage, one can use a precomputed lookup table for $\xi(p)$ and $\eta(p)$). Note that for Class 9, $\delta(p)$ is always zero. This step reduces the size of a lookup table by a factor of 8.

Topological Classification

The objective of topological classification is to uniquely determine the topological class of each voxel in a surface representation of the 3D network. To explain this concept in continuous 3-space $\mathfrak{R}^3$, let $S\mathfrak{R}$ be the union of a finite number of surfaces and curves, each having a finite area or length in $\mathfrak{R}^3$ (FIG. 5(a)). It is interesting to note that a point in $S\mathfrak{R}$ can be classified depending on its local topological property in $S\mathfrak{R}$. For example, in a sufficiently small neighborhood of a point, $p_s$, on a surface, removal of $p_s$ always creates a tunnel. For a point, $p_{ss}$, on a junction of surfaces, it creates multiple tunnels. It creates exactly two objects for a point like $p_c$ on a curve, and multiple objects for a point like $p_{cc}$ at the junction of curves. At a junction of surface and curve, like $p_{sc}$, it creates multiple objects and one tunnel. However, the classification is not so straightforward in a digital space.

Figure 5:
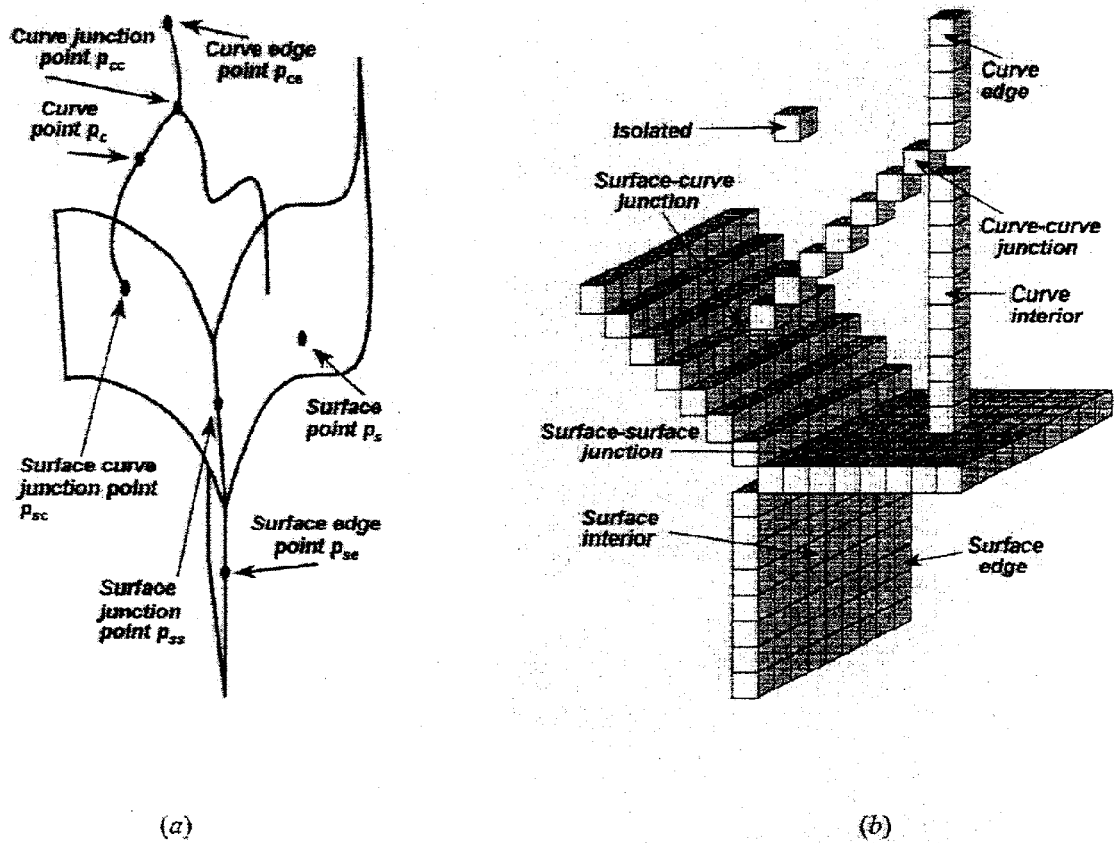
FIGS. 5(a) and 5(b) graphically illustrate possible topological classification in a surface and curve representation.

The classes determined by classical digital topological analysis (Saha et al., 1996) are isolated voxels (I-type), curve interiors (C-type), curve edges (CE-type), curve-curve junctions (CC-type), surface interiors (S-type), surface edges (SE-type), surface-surface junctions (SS-type), and surface-curve junctions (SC-type; FIG. 5(b)). In addition to these classes, the concept of profile elements (PI- and PE-types) have been introduced (Saha 2000A; Gomberg et al., *IEEE Trans. Med. Imaging* 19(3) (2000A); Wehrli et al., *J. Bone Mineral Research*, submitted 2000). These profile type structures are flat, ribbon like structures that, for example, can lead to classification as a double row of SE-type voxels with no adjacent surfaces (S-type) as in FIG. 6. The method for detecting these profile elements is described at the end of this section.

Figure 7:
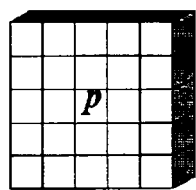
FIGS. 7(a)–7(d) graphically exemplifies situations in which local topological parameters fail to uniquely classify different architectures. As shown in both 7(a) and 7(c), the local topological parameters of p are the same. The neighborhood of p is shown as excluded in FIGS. 7(b) and 7(d), respectively.
Figure 7:
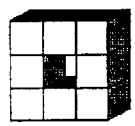
Figure 7:
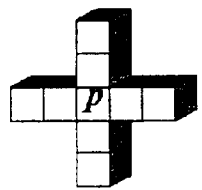
Figure 7:
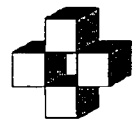

After $\xi(p)$, $\eta(p)$, and $\delta(p)$ have been determined for each voxel in a surface representation of the trabecular bone network, it is possible to proceed to the three-step topological classification, which makes the method simpler to understand and more efficient to implement. Furthermore, the classification is divided into three distinct steps because the local topological parameters of a single voxel in some cases cannot uniquely determine the topological class. For example, given the two surface representations in FIG. 7, the local topological parameters of p in FIGS. 7(a) and (c) are identical (when p is considered as marrow): one object, one tunnel, and no cavities ($\xi$, $\eta$, $\delta$). However, in FIG. 7(a), p is a surface element and in FIG. 7(c), p is a junction of two curves. The unique classification of p can be determined by looking at the parameters of the neighboring voxels to p. The neighbors of p in FIG. 7(a) have ($\xi$, $\eta$, $\delta$)=(1, 1, 0), whereas those in FIG. 7(c) have (($\xi$, $\eta$, $\delta$)=(2, 0, 0).

The three steps of topological classification are: (1) determination of the local topological type, (2) the initial classification based on these types, and (3) the final classification to detect some junction cases and profiles (Saha et al., 2000A; Saha et al., *Internat'l J. Imaging Systems and Technology*, 11:81–90 (2000B); Gomberg et al., 2000A) each of which is herein incorporated by reference). The first step determines the initial topological type (Table 1), which, as demonstrated above, cannot always uniquely determine the topological class. More specifically, $T_1$, $T_3$, $T_4$ give unique initial voxel classifications, whereas $T_2$, $T_5$, $T_6$, $T_7$, $T_8$ give two or more initial voxel classifications.

TABLE 1

Topological Type Table.

| $\xi(p)$ | $\eta(p)$ | $\delta(p)$ | Initial Type | Possible Initial Classification |
|---|---|---|---|---|
| 0 | 0 | 0 | $T_1$ | 1-type |
| 1 | 0 | 0 | $T_2$ | SE-type or CE-type |
| 2 | 0 | 0 | $T_3$ | C-type |
| >2 | 0 | 0 | $T_4$ | CC-type |
| 1 | 1 | 0 | $T_5$ | S-type or CC-type |
| >1 | ≧1 | 0 | $T_6$ | S-type, SC-type or CC-type |
| 1 | >1 | 0 | $T_7$ | S-type, SC-type or CC-type |
| 1 | 0 | 1 | $T_8$ | S-type, SC-type or CC-type |

Figure 8:
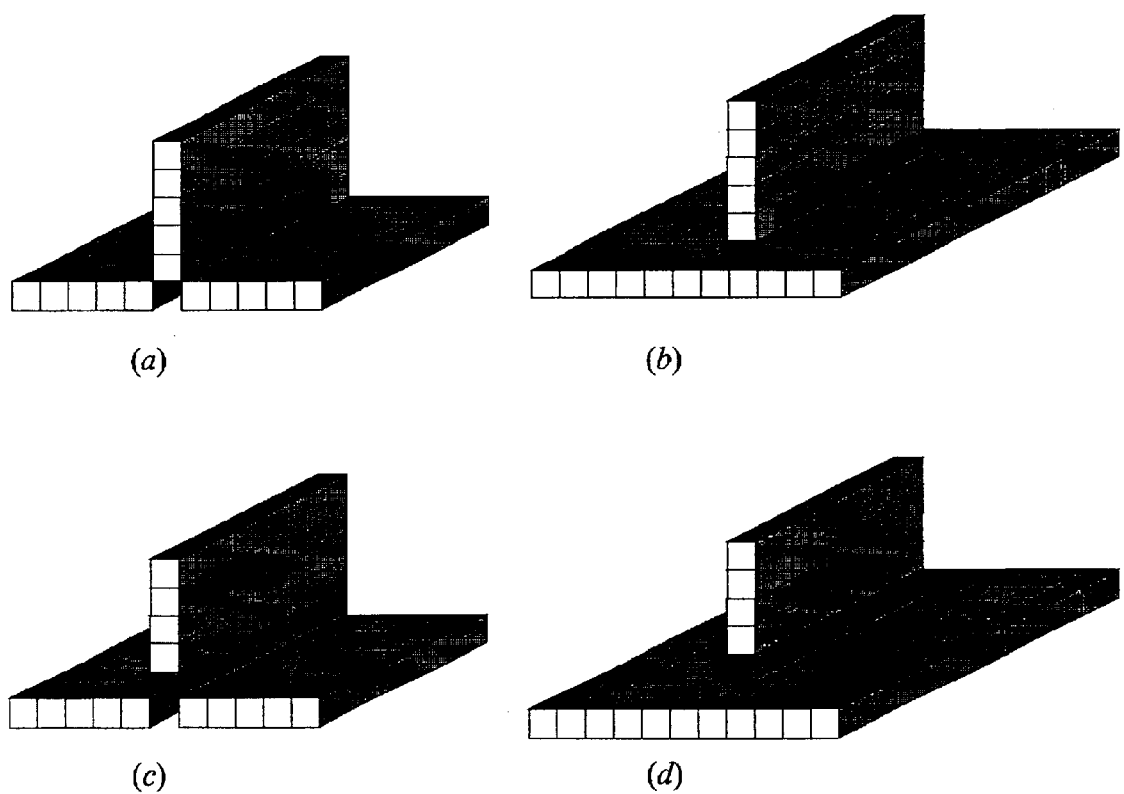
FIGS. 8(a)–8(d) graphically depict extension of SS-lines (SS-type voxels are shown by dotted voxels).
Figure 9:
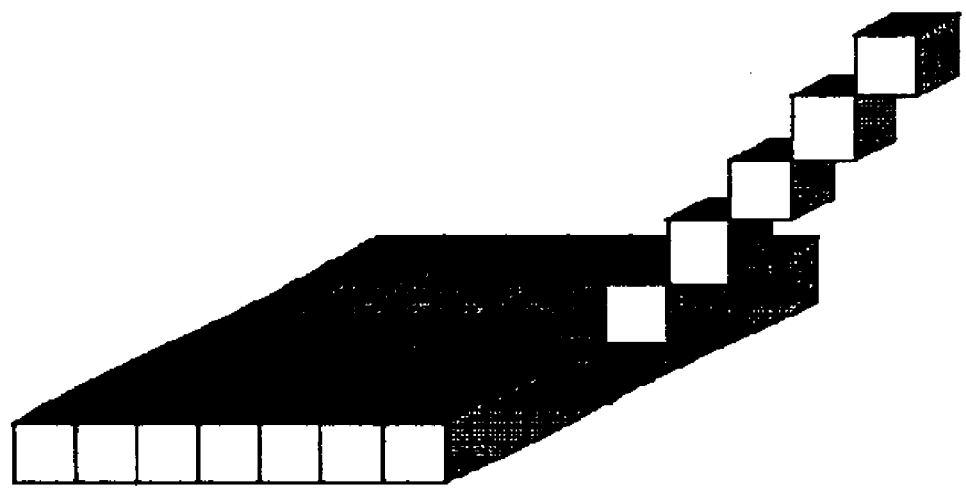
FIG. 9 graphically depicts that the SC-type voxel (shown by dotted cube) cannot be detected using Tables 1 and 2.
Figure 10:
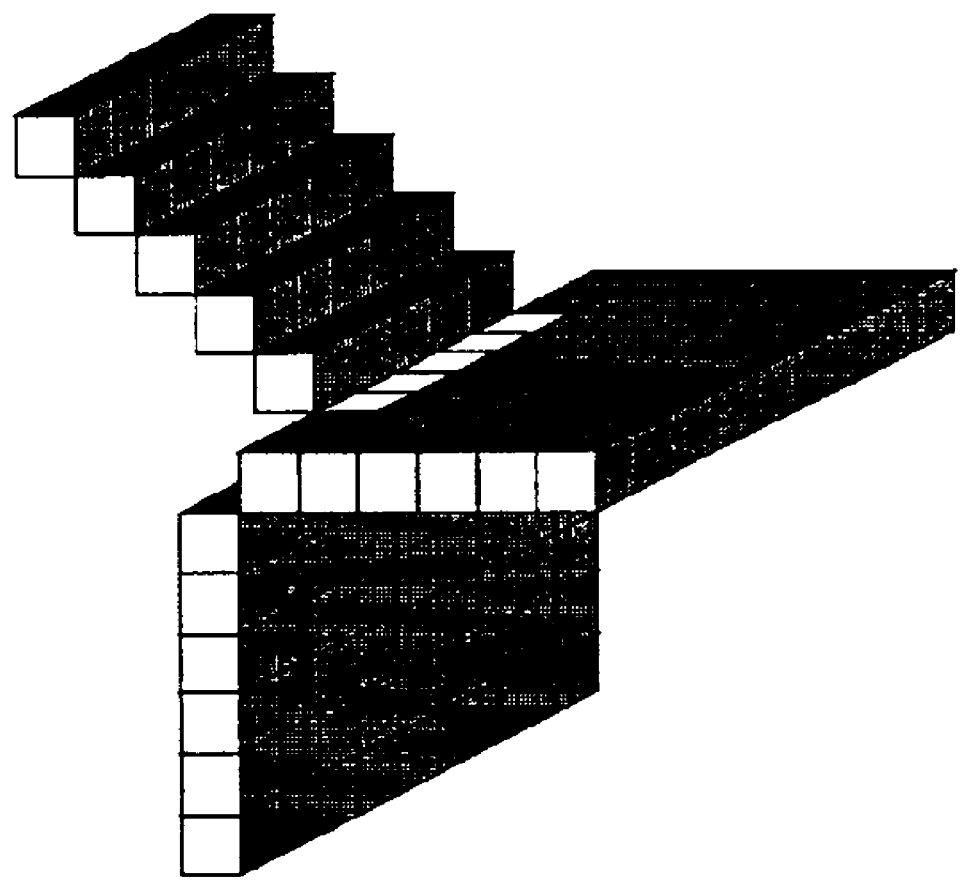
FIG. 10 graphically exemplifies that an extension SS-line (SS-type voxels are shown by dotted voxels) at the end is not needed.

During the second step, the 26-neighborhood is reviewed of any voxel not uniquely classified by Table 1, and Table 2 is used for the initial classification. After the initial classification, the process is complete except for determination of profile elements (FIG. 6) and possible corrections at some surface junctions (See, FIGS. 8, and 9). FIG. 8 illustrates the problem of extension of SS-lines (a 26-path of SS-type voxels). In FIGS. 8(a) and 8(b), the SS-line should be extended to reach the surface edges as shown in FIGS. 8(c) and 8(d), respectively. Care must be taken in extending SS-lines. This is because in another example (FIG. 10), the SS-line should not be extended at the ends. In FIG. 9, the curve is 26-connected to the surface, but the junction voxel has not been classified as SC-type.

TABLE 2

Initial classification table.

| Initial Type | Neighborhood Analysis | Initial Classification |
|---|---|---|
| $T_2$ | Exactly one bone neighbor | CE-type |
| $T_2$ | More than one bone neighbor | SE-type |
| $T_5$ | All bone neighbors are $T_3$ or $T_4$ | CC-type |
| $T_5$ | Not all bone neighbors are $T_3$ or $T_4$ | S-type |
| $T_6$ | All bone neighbors are $T_3$ or $T_4$ | CC-type |

TABLE 2-continued

Initial classification table.

| Initial Type | Neighborhood Analysis | Initial Classification |
|---|---|---|
| $T_6$ | Some (not all) bone neighbors are $T_3$ or $T_4$ | SC-type |
| $T_6$ | No bone neighbor is $T_3$ or $T_4$ | SS-type |
| $T_7$ | All bone neighbors are $T_3$ or $T_4$ | CC-type |
| $T_7$ | Some (not all) bone neighbors are $T_3$ or $T_4$ | SC-type |
| $T_7$ | No bone neighbor is $T_3$ or $T_4$ | SS-type |
| $T_8$ | All bone neighbors are $T_3$ or $T_4$ | CC-type |
| $T_8$ | Some (not all) bone neighbors are $T_3$ or $T_4$ | SC-type |
| $T_8$ | No bone neighbor is $T_3$ or $T_4$ | SS-type |

Neighboring voxels are 26-adjacent bone voxels. This step resolves ambiguities from the initial type determination, but still requires refinement of some junction cases and determination of profile type voxels.

A. Extension of SS-Lines.

Extensions of SS-lines require looking at the topology of surface edges around the end-points of the SS-lines. Ideally, a surface edge forms a simple closed curve when there is no surface-surface junction; otherwise, this closed curve will be broken by the SS-line. Because the first two classification steps might not detect the end-points of these SS-lines, these points are classified as SE-types. If any of the SE-type voxels near the end-points of SS-lines form junctions between SE-lines (FIG. 8(a)), or are end-points of SE-lines (FIG. 8(b)), but have not been classified correctly, they are changed to SS-type voxels. The following definitions and algorithm will find these misclassified voxels. Let $S_{SE}$ denote the set of all SE-type voxels in the surface representation. Let p be an end voxel of an SS-line. Note, an end voxel of an SS-line has at most one 26-adjacent SS-type voxel. So the single SS-type voxel in $N^*(p)$ will be denoted $p_{SS}$, and let $Q_S$ denote the set of all S-type voxels in $N^*(p)$.

Algorithm 1:

FOR every SE-type voxel $q \in N^*(p) - N^*(p_{SS})$:

IF number of 26-objects in $S_{SE} \cap N^*(q)$ is >2 OR there is a tunnel in $S_{SE} \cap N^*(q)$ THEN flag q;

ELSE IF number of 26-objects in $S_{SE} \cap N^*(q)$ is exactly 1

AND $\exists r \in Q_S \cap N^*(q) - N^*(p_{SS})$ such that $|q-r|<|q-p|$

THEN flag one of the nearest r to q

All flagged voxels are reclassified as SS-type voxels. If the algorithm is executed on FIGS. 8(a) and 8(b), the result is FIGS. 8(c) and 8(d), respectively.

B. Finding Junctions Between Curves and Surfaces.

When a curve meets a surface, there will be a surface-curve junction in between them. After the second classification step, some of these surface-curve junctions will not be detected. To correct this we must look at surface voxels with neighboring curve voxels and make corrections as needed. The algorithm is as follows: Let p be a C-type or CC-type voxel and let Q be the set of S-type, SC-type and SS-type voxels in $N^*\square p\square$. Let $O_1, O_2, \ldots O_n$ be the 26-objects in Q. If $O_i$ has no SC-type or SS-type voxels, the nearest voxel to p in $O_i$ is reclassified as a SC-type voxel.

C. Profile Elements.

Figure 6:
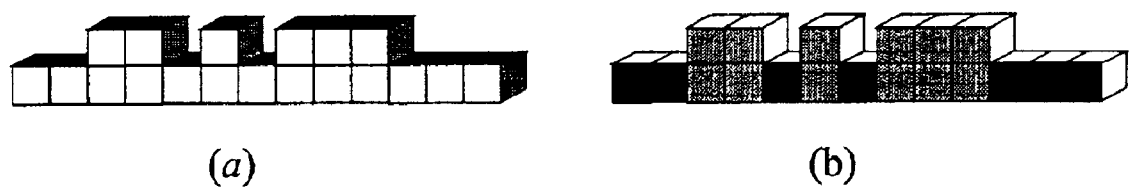
FIGS. 6(a) and 6(b) graphically exemplify profile elements.

One major structural type missing from classical digital topology is the concept of a profile-type element. Because of the biological variation of trabecular structures and the erosion process that converts plates to rods, the topological classification needs to identify these correctly. To allow these classifications, the concept of profiles has been introduced that include profile edges and interiors. For example, because rod-like biological structures are rarely perfect cylinders, and the thresholding process of partial BVF voxels will produce further cross-sectional distortions, the resulting surface skeleton representation may have curves that consist of two-voxel width surfaces (FIG. 6). The resulting topological analysis classifies these curves as double rows of surface edges.

Because a surface edge, by definition, must be adjacent to a surface, any surface edge that is not should be classified as a profile edge (PE-type). Additionally, isolated surface voxels surrounded by surface edges can be considered a profile interior (PI-type) as well. The preferred embodiment of profile characterization is the establishment of a series of profile grades that describe the profile width. This embodiment can be extended to the analytical case of a surface distance transform method.

A profile edge-type (PE-type) voxel is defined as any SE-type voxel, p, with no S-type, SC-type, or SS-type voxels in $N^*(p)$. In voxel counting, two PE-type voxels will be counted as one C-type voxel. PE-type voxels generally appear in pairs across the curve direction because a single voxel would have been classified as a curve point.

Once the topological classification has been completed, the results need to be further evaluated to account for volume of interest (VOI) edge artifacts. Edge artifacts result from the method identifying edges in the trabecular structure caused by the VOI boundaries. These artificial edges are further modified by of the skeletonization process. During each iteration of the skeletonization process, the edges propagate one voxel layer into the structure at most. Therefore, for n skeletonization iterations, the VOI used for voxel classification counting would need to be eroded using a mask size of 2n+1.

Finally, to compare the voxel counts from different subjects, the classification counts need to be normalized to the VOI volume. The final classification density can be calculated by a straightforward division of the weighted classification count by the total VOI voxel count.

EXAMPLES

The invention is further described by example. The examples, however, are provided for purposes of illustration to those skilled in the art, and are not intended to be limiting. Moreover, the examples are not to be construed as limiting the scope of the appended claims. Thus, the invention should in no way be construed as being limited to the following examples, but rather, should be construed to encompass any and all variations which become evident as a result of the teaching provided herein.

Description of the Method

The digital topological analysis method begins with bone volume fraction (BVF) maps of the trabecular network to be analyzed. These maps can be generated from any imaging modality, such as micro-CT, CT, pQCT, micro-MRI etc, after suitable preprocessing to produce BVF maps. These BVF maps are threshholded, and subsequently skeletonized to a surface representation before topological classification.

Figure 11:
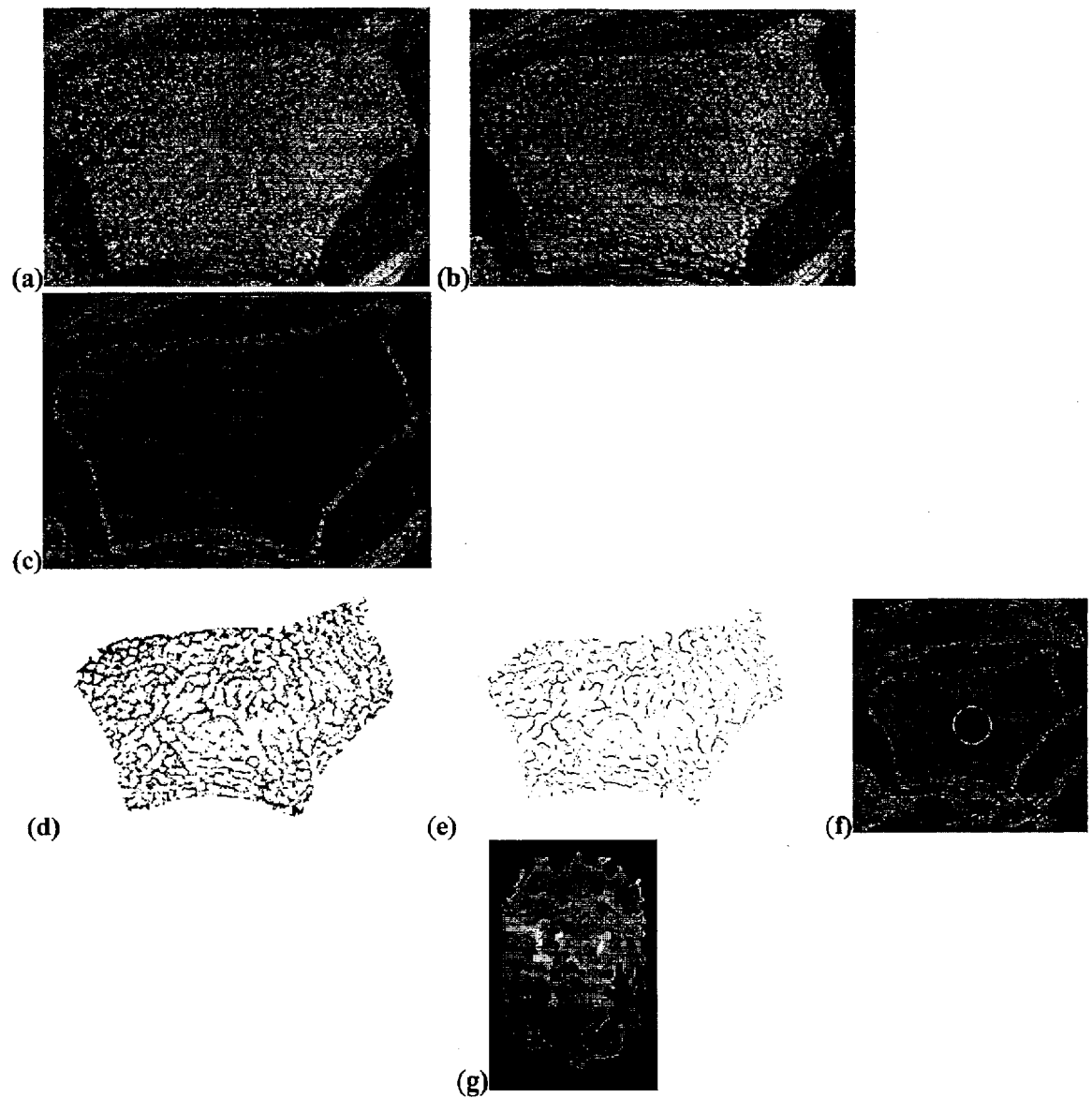
FIGS. 11(a)–11(g) photographically depict the various stages involving acquisition, processing and analyses of the trabecular bone images: (a) raw data (shown as FIG. 11(a)); (b) motion corrected (shown as FIG. 11(b)); (c) bone volume fraction map following histogram deconvolution (shown as FIG. 11(c)); (d) subvoxel processed (shown as FIG. 11(d)); (e) map after topological classification (surfaces in black, curves in gray) (shown as FIG. 11(e)), (f) localization of virtual core (shown as FIG. 11(f)), (g) 3D shaded surface projection of virtual core (shown as FIG. 11(g)). Notably, the arch shaped structure (arrow in FIG. 11(a)) is visible in all images.

The technology of estimating the structural parameter of the trabecular networks is visualized in FIG. 11, involving acquisition, processing and analyses of the trabecular bone images: (a) raw data (FIG. 11(a)); (b) motion corrected (FIG. 11(b)); (c) bone volume fraction map following histogram deconvolution (FIG. 11(c)); (d) subvoxel processed (FIG. 11(d)); (e) map after topological classification (surfaces in black, curves in gray) (FIG. 11(e)), (f) localization of virtual core (FIG. 11(f)), (g) 3D shaded surface projection of virtual core (FIG. 11(g)). Notice that the arch shaped structure (arrow in FIG. 11(a)) is visible in all images. The sThe processing steps for DTA were all performed on a dedicated computer system, following the transfer of the complex k-space and navigator data from the scanner (General Electric Signa Echospeed™) utilizing file transfer protocol (FTP). Step 1, comprises navigator correction and Fourier reconstruction of the 3D spin-echo images (Majumdar et al., 1997. In step 2, noiseless bone volume fraction (BV/TV) maps were generated by means of a histogram deconvolution method. BV/TV was obtained by computing an average over the VOI or different subregions. In step 3, the images were resolution-enhanced using a method termed "subvoxel processing" (Wehrli et al, 1998B).

At this stage, images high resolution BV/TV maps of 69×69×87 $\mu m^3$ voxel size were ready for structural analysis. The processed data files reached up to 20 Mbytes in size. To accommodate such large file sizes, the system incorporated file compression, large-capacity hard disks, and CD recorders for archiving. In step 4, all voxels of the subvoxel-processed BV/TV maps were binarized, skeletonized and topologically classified. This operation determined the local topological class of each voxel (DeHoff et al., 1972)(e.g. surface, curve, junction, etc.) as a means to quantitatively characterize the trabecular network. Finally, a projection image from an automatically selected cylindrical region ("virtual bone biopsy") was created to provide a qualitative visual impression of trabecular network integrity.

System control and interface was written in IDL (Research Systems, Inc. Boulder Colo., USA), but the actual processing was distributed between the IDL system, command-line programs, and a Unix-based processing subsystem accessed through FTP and telnet connections. This system allowed integration of algorithms from multiple investigators working in different environments and will facilitate the addition of new analytical techniques as they are developed. The results were compiled into a Microsoft Excel spreadsheet and transferred automatically to a Microsoft Word document for display and printing.

The entire system was designed for high throughput by distributing the workload among multiple computers (PC, Mac, or Unix) on a network and consolidating the spreadsheet results on a single machine, enabling the large scale processing needed for epidemiological studies and clinical trials. The final output of the system is a multi-page (2-page) clinical report that provided a qualitative and quantitative summary of the subject's bone quality.

Imaging.

As part of the reduction to practice, the topological method was applied to three types of data: synthetic, trabecular bone specimen, and in vivo images. Synthetically data was generated to demonstrate the accuracy of the method. The image data sets from specimens of the human distal radius, previously studied by means of spatial autocorrelation analysis (Hwang et al., 1997), were re-examined to assess the potential of topological analysis as a means of predicting the mechanical properties of the trabecular networks. Finally, trabecular bone images acquired in vivo from volunteers and patients of varying skeletal status were used to show reproducibility and application to cross sectional studies.

Since current in vivo MRI resolution is on the order of the trabecular thickness, accuracy of the topological parameters as a function of structure resolution was of particular interest. To create synthetic images, rod-like and plate-like structures were generated through semi-regular grid points, with uniform random variations in position, that mimic the variations seen in vivo, using cubic spline curves and surfaces (IDL, Research Systems, Inc., Boulder, Colo.). Partial volume mixing was mimicked and Rician noise (Gudbjartsson et al., *Magnetic Resonance Med.* 34:910–914 (1995) (signal-to-noise ratio≈15) was added to all synthetic images to simulate the noise characteristics of magnitude in vivo MR images. These synthetic images contained known counts of surface and curve voxels and the results of the topological analysis were compared with these known quantities to evaluate the absolute accuracy of the method.

The high-resolution cadaveric specimen images (n=22, 8 females, 14 males) had an isotropic voxel size of 78×78×78 $\mu m^3$, a resolution at which 3D trabecular micro-architecture is preserved. The ages and elastic moduli (in the axial direction) for these specimens ranged from 53 to 87 years old and 104 to 712 MPa, respectively. These images displayed a wide range of morphologies from predominantly rod-like to predominantly plate-like architecture. The specific question addressed was whether topological parameters would be able to predict Young's (YM) modulus for uniaxial loading. Details on pulse sequence and imaging methods can be found in Hwang et al., 1997.

In another study, in vivo images were acquired as part of an ongoing clinical study to evaluate the architectural changes that occur during osteoporotic bone loss. These images of the distal radius were acquired on a clinical magnetic resonance scanner (1.5-T General Electric Signa™, Milwaukee, Wis.). A custom-designed 3D-FLASE spin-echo pulse sequence (Ma et al., *Magnetic Resonance Med.* 35:903–910 (1996)) (radio-frequency pulse flip angle=140°, TR=80 msec, TE=7.7–11.4 msec, 512×256×32 matrix size) was used with a home-built transmit-receive RF coil encompassing the distal end of the forearm (See also description provided in Example 2). For each subject, 32 contiguous images were acquired at 137×137 $\mu m^2$ in-plane resolution and 350-$\mu m$ slice thickness (137×137×350 $\mu m^3$). In addition, the pulse sequence was equipped with navigator echoes to correct for translational motion of the wrist during scanning (Song et al., *Magnetic Resonance Med.* 41:947–953 (1999)).

Preprocessing.

All images were preprocessed by deshading and noise reduction using a histogram deconvolution method (Hwang et al., 1999). See also, the methods as described in Example 2. The resulting images represent the BVF at each voxel location. The VOI was manually outlined for each slice, and adjusted to exclude areas containing acquisition artifacts. For in vivo images, resolution was enhanced using a subvoxel classification technique similar to the one described by Wu et al., (*Magnetic Resonance Med.* 31:302–308 (1994)) resulting in a final voxel size of 68×68×86 $\mu m^3$. In this manner, an in-slice and across-slice continuity of the trabecular network was achieved, which aided the preservation of topology during the skeletonization procedure.

Thresholding and Skeletonization.

As pointed out previously, topological parameters are derived from a surface representation of a binarized trabecular bone network. This means that all volume objects must be reduced to 1D or 2D structures, and there can be no bulk elements present in the digital image, which is accomplished by thresholding and skeletonizing. To determine the optimal threshold for binarization of the images, BVF thresholds from 0.01 to 0.99 were applied to the BVF images from ten subjects of varying skeletal status, as determined by DEXA BMD of the lumbar spine (L2–L4), using a Lunar DPX dual-energy X-ray absorptiometer (Lunar Corporation, Madison, Wis.). These binarized images were thinned, and the number of voxels in the surface skeleton representation counted. The averaged consecutive change in total skeleton voxel counts versus BVF threshold for all subjects revealed a local minimum at 0.25–0.40 BVF threshold. In this region, the skeleton structure changes minimally as a function of threshold, and therefore, a constant BVF threshold of 0.25 was used for all images.

After thresholding, the images were skeletonized using a published algorithm (Saha et al., *Pattern Recognition* 30:1939–1955 (1997)) because of its robustness to noise and rotation.

Topological Classification and Analysis.

Topological theory determines the local connectivity properties of each skeletonized voxel, and hence the topological classification as described above. The region of trabecular bone ("VOI mask") being analyzed was morphologically eroded by twice the approximate trabecular thickness to eliminate edge effects. Each topological class count was then combined separately and normalized to the total volume of the eroded VOI mask. These results were dimensionless topological densities. In one embodiment of the DTA technique, the local orientation and scale information were used to weight each voxel to account for the rotational and scale dependence of the topological parameters.

To reduce the complexity of the data analysis, classification counts of the similar type elements were combined. The surface edge and surface interior voxels were counted together as surface voxels; similarly, both the edge and interior voxels of curves were counted as curve voxels. One half of the profile voxel counts was added to the curve counts. In addition, all of the different types of junction voxels were counted as junction voxels. The operation provided four different categories of voxels: isolated, curve, surface, and junction voxels.

These topological densities were combined into indices that provide an indication of network strength, such as surface to curve ratio and erosion index (TABLE 3). Using a surface-profile-curve erosion cascade model, an 'erosion index' was defined as the ratio of all topological parameters expected to increase with erosion (C-type, CE-type, SE-type, PE-type, and CC-type) to all those that are expected to decrease by erosion (S-type and SS-type).

TABLE 3

Definition of topological parameters.

| DENS | Topological skeleton density | Fraction of all bone voxels in the skeleton |
|---|---|---|
| CE | Curve edge voxel density | |
| SE | Surface edge voxel density | |
| C | Curve interior voxel density | |
| S | Surface interior voxel density | |
| CC | Curve-curve junction density | |
| SC | Surface-curve junction density | |
| SS | Surface-surface junction density | |
| PE | Profile edge voxel density | |
| PI | Profile interior voxel density | |
| SURF | All surface voxel density | S + SE + SS |
| CURV | All curve voxel density | C + CC + PE/2 |
| JUNC | All junction voxel density | SC + SS + CC |
| SCR | Surface to curve ratio | SURF/CURV |
| EI | Topological erosion index; ratio Parameters expected to increase divided by those expected to decrease upon skeleton erosion | (C + CE + SE + PE + CC)/ (S + SS) |

Visualization.

"Virtual bone biopsies" were generated for displaying projections of cylindrical cores extracted from the in vivo cancellous bone volumes. A longitudinal cylindrical VOI mask was automatically generated (diameter of 5.5 mm) through all slices containing bone. This VOI was positioned concentrically with the center of mass of the cancellous volume. Bone voxels were extracted from the BVF maps using a 0.25 threshold. To eliminate artifactual (edge artifacts) bone "fragments" left in the VOI, small and disconnected elements of bone were removed using 3D region growing based object analysis. To preserve large bone structures that might happen to be disconnected in the VOI, only objects comprising >5% of the total VOI volume were retained for visualization. Median filtering was performed on the images to smooth the bone marrow interfaces and produce the best visual results. The "biopsies" were visualized using depth-queued nearest voxel projection (IDL, Research Systems, Inc. Boulder, Colo.).

EAMPLE 1

Validation and Applications of the Invention

Validation: Accuracy in Synthetic Images

Analysis of the synthetic images shows that for rod-like structures (i.e. curves) of greater than 0.9 voxel diameter the topological method has an absolute accuracy of 97%. However, at lower structural resolutions, accuracy was seen to decrease rapidly. The increase in classification errors at lower resolutions can be explained by partial volume mixing of low BVF voxels. Since a rod can intersect between one and four voxels within each slice, rods of 0.6 and 0.7 diameters result in maximum voxel BVFs ranging from 0.07 to 0.28 and 0.095 to 0.38, respectively. Recalling that the empirically determined BVF threshold for binarization was 0.25, one would expect that at low rod diameters, many of the low BVF voxels would disappear. At greater rod diameters, BVF increased sufficiently for more elements to survive after thresholding, resulting in increased classification accuracy. The reproducibility for rods was estimated at 0.999 (p<0.0001) as determined by the intraclass correlation coefficient (ICC) (Shrout et al., *Psychological Bull.* 86:420–428 (1979)).

For plates (surfaces), the absolute accuracy was greater than 98% for all plate thicknesses tested, with an ICC for surface counts of 0.99 (p<0.0001). This result was consistent with the findings for the synthetic rod images—the extent of partial volume mixing is key to determining the structural elements that will survive the skeletonization. At a plate thickness of 0.6, the minimum BVF at any plate location was 0.3 (when the plate is equally distributed across two voxels). Since the range of trabecular sizes in normal human bone is 100–150 $\mu$m, the choice of 0.25 as the BVF threshold and an in vivo resolution of 137×137 $\mu$m$^2$ includes most plate-like trabeculae of normal thickness.

EXAMPLE 2

Applications ex vivo to Bone Specimens: Prediction of Elastic Properties of Trabecular Bone These properties were used to ascertain relationships with trabecular network competence of the bone specimens as represented by Young's modulus (YM) using regression analysis (JMP-IN, SAS Institute Inc., Cary, N.C.). Toward this goal Young's modulus data obtained in prior work on human wrist specimens were re-examined. The experiments are detailed in Hwang et al., 1997. In brief, YM was derived from stress-strain curves by uniaxial compression testing of cylindrical trabecular bone samples (9 mm diameter and length) drilled parallel to the long axis of the bone from the ultra-distal radius of 13 cadavers (Hwang et al., 1997).

Figure 12:
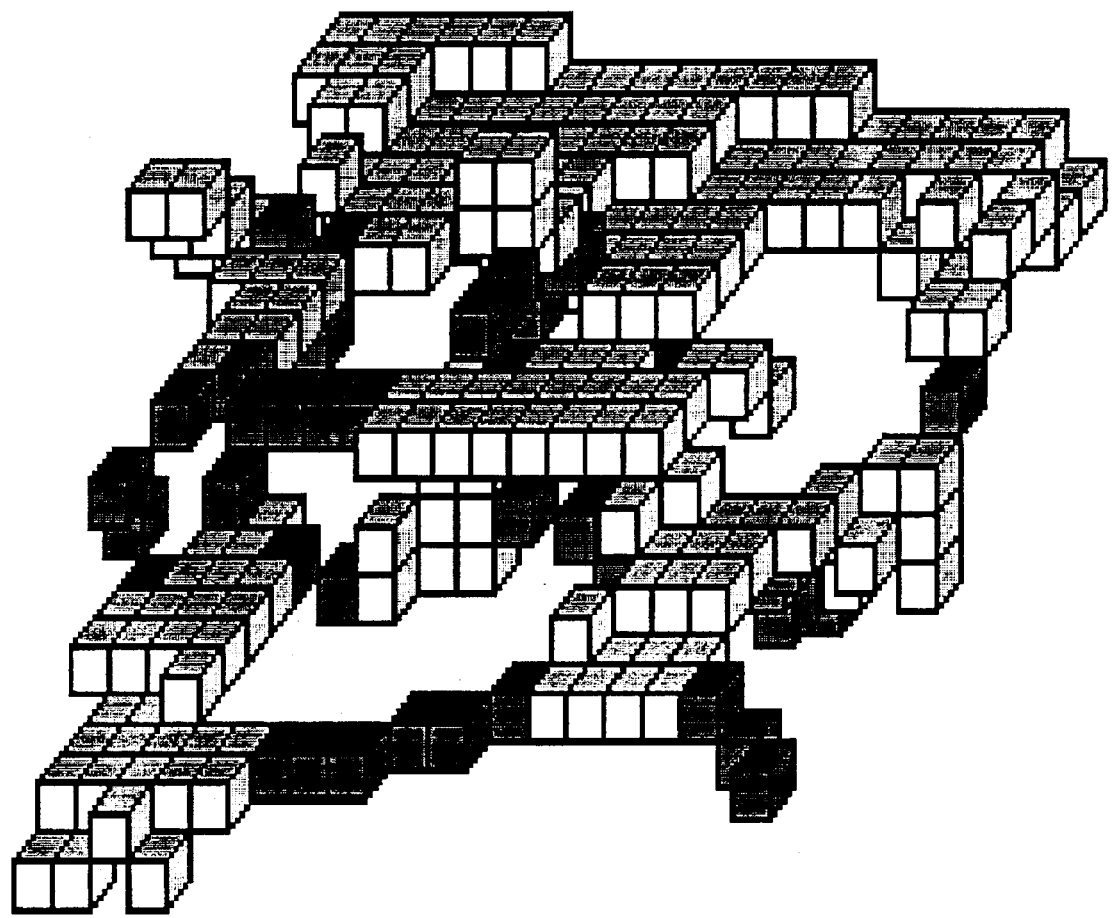
FIG. 12 graphically depicts a voxel display of topological classification, which results in skeletonized trabecular bone showing surface and curve voxels (light and dark, respectively). The data represent a subregion of 10×20×20 voxels taken from an image obtained at $(78 \mu m)^3$ voxel size.
Figure 13:
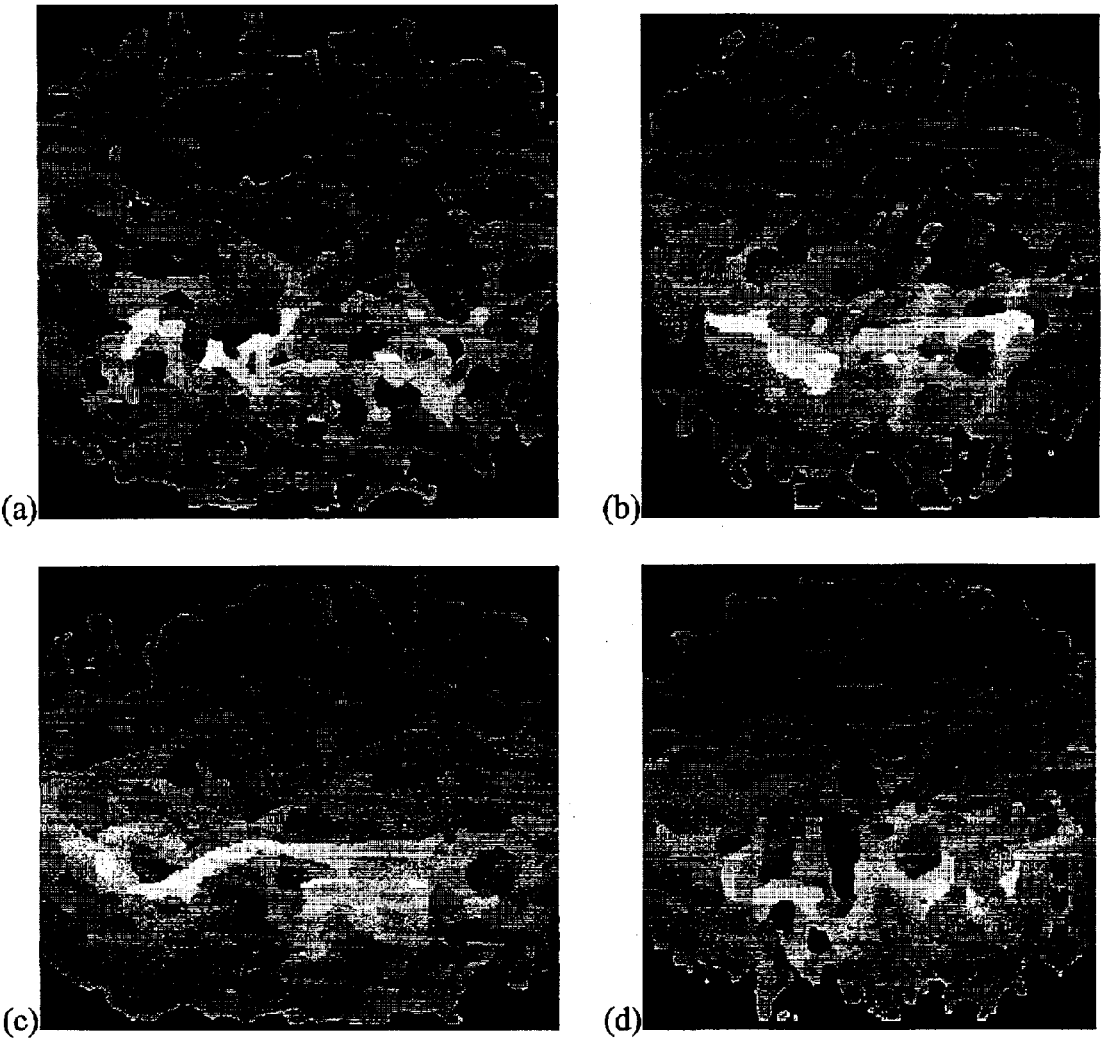
FIGS. 13(a)–13(d) photographically depict qualitative examples of plate-like and rod-like networks.

The accuracy of topological classification is illustrated in a small region of an ex-vivo surface skeleton image, displayed as a voxel projection in FIG. 12, clearly showing the correct classification of surface and curve structures. The projection images of the in vitro data (FIG. 13) are arranged in order of increasing visual "plate-likeness." FIG. 13(a) depicts a highly rod-like network in a 74 year old female. FIG. 13(b) depicts a medium rod-like network in a 53 year old female. FIG. 13(c) depicts a highly plate-like network in a 68 year old female. FIG. 13(d) depicts a very highly plate-like network in a 60 year old male. Topological parameters (Table 6) support visual assessment of increasing plate-like morphology and the topological parameters (qualitative ordering). In the four specimens, the surface/curve ratio of FIGS. 13(a)–13(d) was found to increase by more than an order of magnitude. While there was an increase in surface density and decrease in curve density in the same order, each parameter varied far less than their ratio, which provides an indicator of trabecular bone erosion. The final measure, the erosion index, also emphasized the qualitative trends of erosion (rod-versus plate-likeness) seen in the samples, changing from 1.5 in the most plate-like specimen FIG. 13(a) to 0.3 in the most rod-like one FIG. 13(d). It has been shown that erosion of trabeculae results in bone plates changing to rods, which eventually become disconnected (Amling et al., 1996; Parfitt, 1992). The transition phase between plates and rods is most likely a profile-like structure that is topologically unique.

To evaluate whether topological parameters are predictive of YM, linear regression models were tested (Gomberg et al., 2000A). Table 5 shows single-parameter linear regression results, from which it is evident that topological parameters compared favorably with BVF, some even suggesting stronger association with YM.

TABLE 5

Single parameter prediction of elastic modulus (n = 22).
All parameters were global for
the complete volume of interest and have p < 0.001.

| Parameter, type* | $R^2$ | Correlation |
| --- | --- | --- |
| Erosion index, topo. | 0.67 | Negative |
| PE norm, topo. | 0.66 | Negative |
| Surface/curve, topo. | 0.59 | Positive |
| BVF, scale | 0.57 | Positive |
| S norm, topo. | 0.51 | Positive |
| Surface, topo. | 0.46 | Positive |

*Scale or topological (topo).

A statistical test to determine whether the difference in the correlation coefficients was significant did not show this to be the case, presumably due to lack of sufficient power (low number of samples, n=22). The erosion index was found to be the strongest single linear predictor of YM ($r^2=0.67$; p<0.0001).

The data emphasize the architectural contribution to cancellous bone competence. A number of investigators have reported improvements in modulus or strength prediction by incorporating measures of architecture into multi-variate models involving BVF or BMD (Goulet et al., 1994; Siffert et al., 1996); Goldstein et al., *Calcif. Tissue Internat'l* 53:S127–133 (1993); Hodgskinson et al., *Proc. Inst. Mech. Eng, pt. H,* 204:43–52 (1990)) showing that density and architectural parameters accounted for 60–90% of the variance in the modulus and ultimate strength. Gordon et al., 1998, found in nine intact radii that measures of bone mineral density explained approximately 50% of the variability with load ($0.52<r^2<0.57$, p<0.03), while indices relating to the size of the marrow spaces explained an additional 25% to 30% of the variance. Oden et al., 1998, reported that the mean intercept length in the specimen primary axis was strongly associated with failure stress ($r^2=0.85$, p<0.001). BMD was also moderately associated with failure stress ($r^2=0.44$, p=0.004). They found that using a stepwise linear multiple regression analysis, the strongest predictor of failure stress was a combination of BMD, specimen orientation angle, and mean intercept length ($r^2=0.91$).

EXAMPLE 3

In Vivo Applications to Patients

Figure 14:
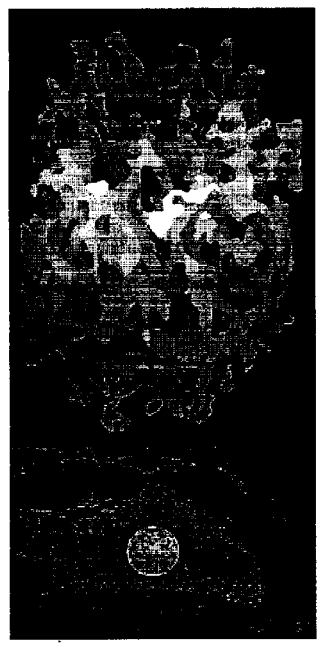
FIGS. 14(a)–14(c) photographically depicts in vivo MR projection images of cancellous bone from the metaphysics of the human radius at $137 \times 137 \times 350 \ \mu m^3$ from three subjects. Topological parameters show increasing surface and decreasing curve densities from FIGS. 14(a) to 14(c), respectively—surface-curve ratios are 5.9, 7.2, and 11.9, and erosion indices are 1.22, 1.07, and 0.72. The cross sections shown directly below each projection, depict the cylindrical cores corresponding to each MR image.
Figure 14:
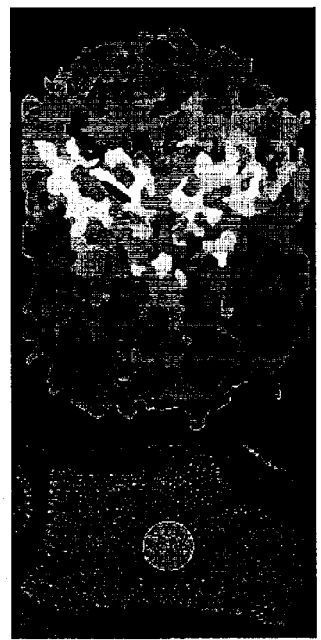
Figure 14:
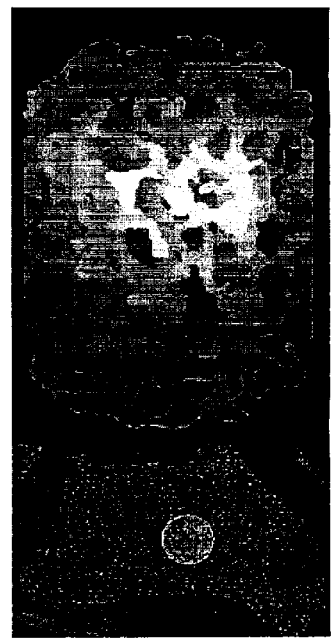
Figure 15:
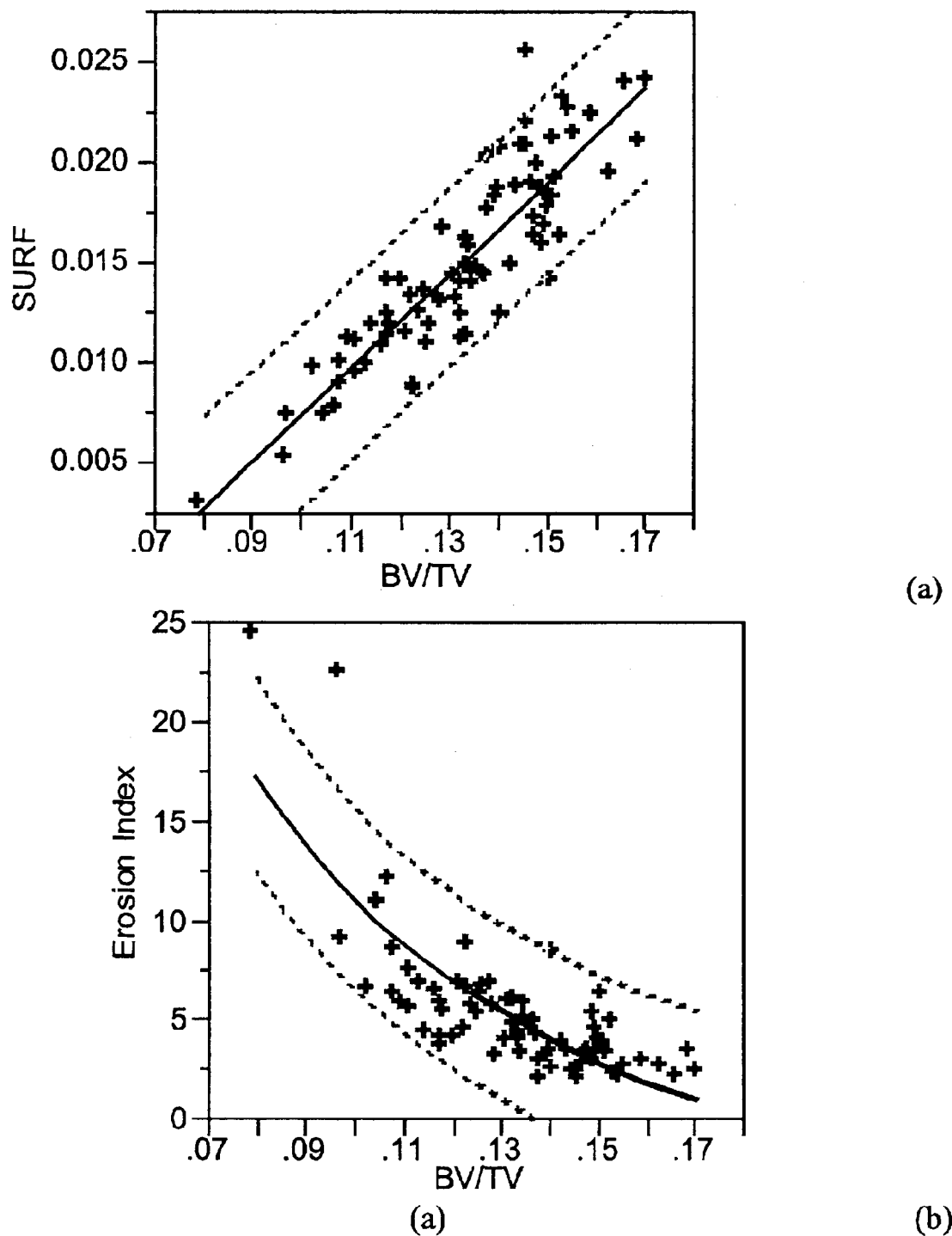
FIGS. 15(a) and 15(b) graphically depict trabecular bone volume fraction, BV/TV, versus DTA structural parameters: a) surface voxel density (SURF) (shown in FIG. 15(a)); b) erosion index (E1) (shown in FIG. 15(b)). Correlation coefficients for both regressions were 0.89.

Of particular medical significance is the application of topological analysis to patients with bone disease, which requires processing of images acquired in vivo. FIG. 14 shows three subjects of varying age and correspondingly different architectures. The images in FIG. 14(a) display both numerically and visually a pronounced rod-like architecture, unlike those in FIG. 14(c), which were predominantly plate-like. These differences in morphology can be understood considering that the images in FIG. 14(a) are from a 73 year old woman, whereas the images in FIG. 14(c) are from a 30 year old man. The images in FIG. 14(b), which display a mixed architecture of plates and rods, were from a 49 year-old woman. The topological parameters parallel the same trend seen visually, with surface-curve ratios of 5.9, 7.2, and 11.9, and erosion indices of 1.22, 1.07, and 0.72. The cross sections shown directly below each projection, show that the cylindrical cores were taken from the same relative location, despite the obviously different morphologies.

EXAMPLE 4

Association Between DTA Parameters and Fracture

In related work demonstrating the method's clinical potential, DTA has been conducted on in vivo MR microimages of trabecular in a cohort of patients of varying bone mineral density and vertebral fracture status (Wehrli et al., *J. Bone Mineral Research*, in press, herein incorporated by reference). DTA was used to quantify the architecture of the trabecular bone network in the distal radius of women of widely varying bone density using 3D $\mu$-MRI, and the findings were compared with DEXA BMD. Specifically, the following hypotheses were tested: (i) structural indices in the distal radius, although associated with BMD in the proximal femur and spine, provide additional information, which is not available from bone densitometry; and (ii) the distal radius is an appropriate surrogate site for assessing vertebral deformity status.

The study comprised 79 women (Caucasian: 65, black: 13, Asian: 1; mean age, 54.8±13.0 years; range, 28–76 years). Micro-MRI was performed in the ultradistal radius of the right hand on a General Electric Signa™ 1.5 Tesla commercial MR scanner with a custom-designed transmit-receive birdcage coil, as described above. Subjects were imaged supine with their arms parallel to the body axis. Dual-Energy X-Ray Absorptiometry (DEXA) was performed in the lumbar spine and proximal femur. BMD T-scores were tabulated as calculated on the basis of the manufacturer's reference database.

Vertebral deformity was determined on the basis of the sagittal MR images of the spine acquired as part of the MR protocol (see above) analogous to prior work (Wehrli et al., 1998B; Wehrli et al., *Radiology* 217:527–538 (2000)), and based on the method of Eastell et al. (*J. Bone Miner. Res.* 6:207–215 (1991)). A vertebra was considered fractured if it had any deformity over 15%, as proposed previously (Nelson et al., 1996). In this manner, the 'number of fractures' (NFX) for each subject was determined. To compensate for the different severity of each type of deformity, a weighting scheme (Steiner et al., *Osteoporosis*, Academic Press, San Diego, pp 1019–1050 (1996)) was used that set the relative values for bicon, wedge and comp fractures at 1, 1.5, and 3 respectively. This results in the 'weighted number of fractures' (WNFX).

Finally, a 'spinal deformity index' (SDI) was computed by summing the weighted deformities over most of the T-spine (typically from T4 or T5) and the entire L-spine for each subject. Thereafter, the study population was divided into two groups, a 'fracture' and a 'nonfracture' group by setting thresholds for WNFX (WNFX 1=fracture) and for SDI (SDI 262=fracture). Both classification schemes are subsequently evaluated with respect to the discriminating ability of the MR and DEXA parameters.

The two classification schemes of vertebral deformity described above yielded, after thresholding, 28 and 29 subjects with fractures, respectively, from the pool of 79 patients. When WNFX was used as a criterion for the presence of vertebral deformity, DEXA BMD measured at any one site was unable to distinguish 'fracture' from 'nonfracture', even though the trends suggest the expected lower T-scores to be associated with the fracture group. By contrast, 8 of the 15 topological parameters were found to be significantly different in the fracture group, with the erosion index (p=0.006) and the surface-to-curve ratio (p=0.01) being the strongest discriminators.

Determination of the vertebral 'fractures' by summing all vertebral deformities and setting a threshold on the resulting deformity index, which is a continuous variable, yielded similar results, but the associations were considerably stronger. All BMD sites were significantly lower in the 'fracture' group. Most importantly, however, 10 of the 15 DTA parameters were significantly different in the 'fracture' group. Particularly discriminating are structural parameters that are measures of plate density (S, SE, SURF and SCR), that are all lower in the 'fracture' group (p<0.001) supporting the view that osteoporotic bone loss is associated with loss of plate-like bone.

Figure 16:
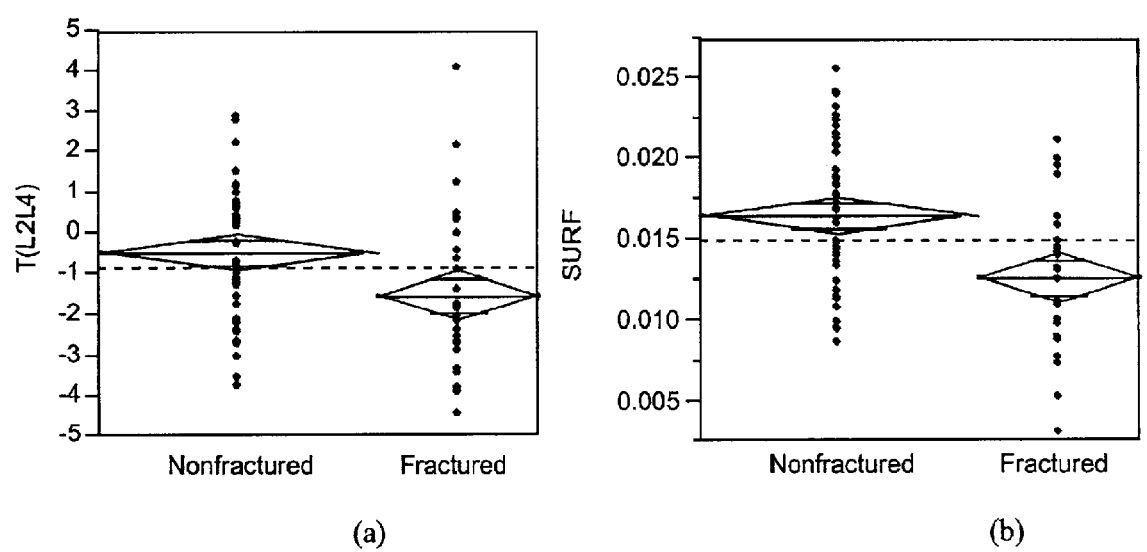
FIGS. 16(a) and 16(b) graphically depict scatter plots comparing BMD T-Score (average L2–L4).

Scatter plots comparing BMD and SCR as discriminators of the two groups are shown in FIG. 16 (FIG. 16(a) shows the topological surface-to-curve ratio; FIG. 16(b) shows discriminators of fracture). By far the strongest discriminator was PI (profile interior voxel density), which was considerably lower in the 'fracture' group (p<0.0001), indicating that bone loss caused disruption of trabecular struts. This interpretation was further supported by the higher density of curve-edge voxels (CE) in the 'fracture' group, consistent with bone loss leading to generation of 'free ends' or termini.

EXAMPLE 6

Association Between DTA Parameters and Bone Volume Fraction and BMD

It was expected that loss in bone volume typically would be accompanied by topological changes, for example, in bone loss associated with age or due to estrogen deficiency. Therefore, topological parameters parallel, to varying extent, BV/TV at the radius, and also DEXA BMD at both femur and spine. The correlation coefficients, however, indicated that typically 65% ($r^2$=0.35) or more of the variances in structure are unexplained by changes in BMD or BV/TV.

The relationships were stronger between BV/TV and DTA parameters since they relate to comparisons at the same site. The strongest positive associations were found for correlations involving surface voxel densities (SE, S, SC and SS; r=0.82–0.92), suggesting that decreases in bone volume occur at the expense of plates, i.e., supporting the notion of fenestration due to inhomogeneous erosion.

Among the three significant negative correlations were those involving curve-edge density (CE) and the erosion index, which represents the ratio of the sum of all curve voxels over the sum of all surface voxels (EI; r=−0.74 and −0.71, respectively). The increase in curve-edge voxel density with decreasing BV/TV was consistent with the disruption of trabecular struts and the creation of "free ends." The associations between DTA parameters and BMD at the femoral and vertebral sites were analogous in sign and relative magnitude, but were generally weaker than the corresponding intra-site correlations. This finding was plausible considering that DEXA BMD does not represent trabecular volume density, and that BMD at these locations may vary in a site-specific manner.

Of particular interest was the range across which a parameter changes, since this quantity indicated the relative sensitivity of a particular parameter. BMD T-scores in the patients studied varied between about −4 to +4 (or from about 0.7 g/cm² to about 1.6 g/cm²). Likewise, radial BV/TV was found to cover a range from 8% to about 17%, comparable in magnitude to BMD (i.e., ~100%). By contrast, the topological surface voxel density and erosion index varied by a factor, ranging from 6 to 10, respectively. The data, therefore, suggested that structural changes in response to a change in bone volume fraction or BMD were greatly magnified. If measured with sufficient precision, these parameters could assist in detecting small changes in response to treatment and for following progression or regression of disease.

SUMMARY

In conclusion, the present example is believed to be the first in vivo manifestation of the disease-specific conversion of trabecular plates to rods in postmenopausal osteoporosis. The data show that trabecular bone structure analysis, based on a complete voxel-by-voxel characterization of network topology, provides insight into the architectural changes that occur during the pathogenesis of osteoporosis, i.e. the conversion of plates to rods and the disruption of rod-like trabecular elements, hitherto evident only from ex vivo bone biopsy. The strong associations between trabecular structure in the distal radius and the extent of vertebral deformities support the knowledge that impaired integrity of the trabecular network at the distal radius site parallels similar changes in the spine. Further, the range of some of the topological parameters exceeds the changes in terms of bone density or bone volume fraction by nearly an order of magnitude, indicating that the architectural consequences of bone loss are significantly amplified.

Thus, the embodied 3D digital topology method of the invention for quantitatively assessing trabecular bone networks allows a unique determination of the topological identity of each voxel as belonging to a curve, junction, or surface. A detailed evaluation has shown that the algorithm is remarkably robust over a wide range of resolutions as long as image voxel size is sufficient to resolve the structures under investigation. Moreover use of the method on 3D MR microimages of human trabecular bone have demonstrated that the volume densities of parameters, such as the surface-to-curve ratio, are strong predictors of Young's modulus, and that topological parameter densities vary substantially among subjects. Topological analysis offers a method of providing accurate in vivo results and characterization of trabecular bone network integrity. Finally, topology has been shown to be intrinsic to a particular network, and since each voxel is classified uniquely, the embodied method produced localized connectivity information, which along with orientation and scale information (e.g., trabecular thickness) characterized local network strength. Since fractures represent local failure phenomena, topological classification has been identified as a way to predict both the risk and precise location of human trabecular bone fractures.

Thus, the value of using digital topology as a means to quantitatively characterize the 3D architecture of cancellous bone networks has been demonstrated. An important property of the embodied method is its ability to uniquely classify each bone voxel after binarization and skeletonization, therefore providing local connectivity information. The known conversion of plates to rods during normal aging, especially in osteoporosis, appears to be quantitatively measurable from the surface-curve ratio, or the erosion index, as composite parameters directly amenable from analysis. The dramatic variations in cancellous bone morphology occurring among subjects of varying ages and disease states are illustrated with virtual bone biopsies derived from in vivo MR micro images. Accordingly, because the properties of cancellous bone networks are highly dependent on structural organization, the embodied method provides strength assessment in vitro and prediction of fracture risk in vivo.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. The method for noninvasively detecting bone structure, comprising:
    imaging in 3D a region of trabecular bone;
    converting the 3D image into a skeletonized surface representation;
    analyzing the converted image by digital topological analysis;
    classifying each image voxel as a curve, a surface, or a junction; and
    calculating microarchitectural indices from the classified image.

2. The method of claim 1, further comprising calculating the scale and orientation information needed for normalization.

3. The method of claim 2, further comprising combining trabecular orientation and scale information with the step of classifying each voxel to characterize local bone network.

4. The method of claim 1, wherein the classified image shows a conversion of plates to rods and disruption of the rod-like trabecular elements.

5. The method of claim 1, wherein the bone is in vivo.

6. The method of claim 1, wherein the bone is ex vivo.

7. The method for noninvasively determining bone structure of a patient, comprising:
    imaging in 3D a region of trabecular bone of the patient;
    converting the 3D image into a skeletonized surface representation;
    analyzing the converted image by digital topological analysis;
    classifying each image voxel as a curve, a surface, or a junction; and
    calculating microarchitectural indices of from the classified image of the patient's trabecular bone.

8. The method of claim 7, further comprising calculating the scale and orientation information needed for normalization.

9. The method of claim 8, further comprising combining trabecular orientation and scale information with the step of classifying each voxel to characterize local bone network.

10. The method of claim 7, wherein the classified image shows a conversion of plates to rods and disruption of the rod-like trabecular elements.

11. The method of claim 7, wherein condition of the patient's trabecular bone network provides an index of bone disease in the patient.

12. The method of claim 7, wherein steps for determining the structure of the patient's trabecular bone network are repeated at periodic intervals and the resulting determinations compared to measure the progression or regression of osteoporosis in the patient.

13. A method for predicting the risk of fracture or vertebral deformity in a patient according to claim 7.

14. The method of claim 7, wherein the imaged bone region in a patient is selected from a surrogate site selected from the group consisting of the distal radius, distal tibia, mandible or calcaneus.

15. The method of claim 14, wherein microarchitectural imaging and digital topological analysis of trabecular volume densities and bone network of the surrogate site provides an indicia of bone structure throughout the axial skeleton of the patient.

16. A method for predicting the risk of osteoporosis in the patient according to claim 14.

17. The method of claim 14, wherein steps for determining the structure of the patient's trabecular bone network, based upon noninvasive imaging of the patient's surrogate site, are repeated at periodic intervals and the resulting determinations compared to measure the progression or regression of osteoporosis in the patient.

18. A system for noninvasively determining bone structure and strength by digital topological analysis, comprising:
    means for acquiring or reading a 3D image of a region of trabecular bone;
    means for converting the 3D image into a skeletonized surface representation;
    means analyzing the converted image by digital topological analysis;
    means for classifying each image voxel as a curve, a surface, or a junction; and means for calculating microarchitectural indices from the classified image to quantitatively characterize the trabecular bone.

19. A computer program encoded on a computer-readable medium for noninvasively determining bone structure and strength by digital topological analysis, comprising:

means in the medium for acquiring or reading a 3D image of a region of trabecular bone;

means in the medium for converting the 3D image into a skeletonized surface representation;

means in the medium for analyzing the converted image by digital topological analysis;

means in the medium for classifying each image voxel as a curve, a surface, or a junction; and means in the medium calculating microarchitectural indices from the classified image to quantitatively characterize the trabecular bone.

* * * * *